United States Patent
Zhu et al.

(10) Patent No.: US 6,794,541 B2
(45) Date of Patent: Sep. 21, 2004

(54) THIOUREA AND UREA LIQUID-PHASE COMBINATORIAL LIBRARIES: SYNTHESIS AND APOPTOSIS INDUCTION

(75) Inventors: Zhaohai Zhu, St. Paul, MN (US); Chen Mao, St. Paul, MN (US); Rama K. Narla, St. Paul, MN (US); Fatih M. Uckun, White Bear Lake, MN (US)

(73) Assignee: Parker Hughes Institute, St. Paul, MN (US)

( * ) Notice: Subject to any disclaimer, the term of this patent is extended or adjusted under 35 U.S.C. 154(b) by 28 days.

(21) Appl. No.: 09/957,530

(22) Filed: Sep. 19, 2001

(65) Prior Publication Data

US 2002/0103380 A1 Aug. 1, 2002

Related U.S. Application Data

(63) Continuation of application No. PCT/US00/06989, filed on Mar. 19, 2000.
(60) Provisional application No. 60/125,146, filed on Mar. 19, 1999.

(51) Int. Cl.[7] ............................................. C07C 335/00
(52) U.S. Cl. ............................ 564/26; 564/28; 564/29; 564/31
(58) Field of Search ............................ 564/17, 26, 27, 564/28, 29, 31

(56) References Cited

U.S. PATENT DOCUMENTS 5,593,993 A   1/1997  Morin et al. ................. 514/247

FOREIGN PATENT DOCUMENTS

EP         0 816 309        1/1998

OTHER PUBLICATIONS

Bernstein, J.; Yale, H. L.; Losee, K.; Holsing, M.; Martins, J.; Lott, W.A. "The chemotherapy of experimental tuberculosis. III. The synthesis of thiosemicarbazones and related compounds" J.Am.Chem.Soc. 1951, 73, 906–12.*
Bell, et al.; *Journal of Medicinal Chemistry*, vol. 38, No. 25, 1995, pp. 4929–4936.
Boger, D. L.; Jiang, W.; Goldberg, J. *J. Org. Chem.* 1999, 64, 7094–7100.
Cantrell, et al.; *Journal of Medicinal Chemistry*, vol. 39, No. 21, 1996, pp. 4261–4274.
Cohen, J.J., et al. (1992)*Annu. Rev. Immunol.* 10, 267–293.
Dooley, C. T.; Houghten, R. A. *Life Sci.* 1993, 52, 1509.
Fraser, A., Evan, G. (1996) *Cell* 85, 781–784.
International Search Report; PCT/US 00/06989; dated Aug. 24, 2000.
Katritzky et al., *Tetrahedron*, vol. 25, No. 10, 1969, pp. 2265–2267.
Korsmeyer, S.J. (1995). *Trends Genet.* 11, 101–105.
Linette, G.P., Korsmeyer, S.J. (1994) *Curr. Opin. Cell Biol.* 6, 809–815.
Loven et al.; *Berichte Der Deutschen Chemischen Gelsellschaft*, vol. 47, 1914, pp. 1534–1536.
Pinilla, C.; Appel, J. R.; Blanc, P.; Houghten, R. A. *Biotechniques*, 1992, 13, 901.
Steller H., (1995) *Science* 267, 1445–1449.
Thompson, C.B. (1995) *Science* 267, 1456–1462.
Von Braun et al., *Berichte Der Deutschen Chemischen Gesellschaft*, vol. 45, 1912, pp. 2188–2198.
Whyllie A., et al. (1980) *Int. Rev. Cytol.* 68, 251–305.
Zhu D et al., Clinical Cancer Research 4:2967–2976, 1998.
Zhu et al., *Book of Abstracts, 217th ACS National Meeting*, Abstract MEDI–023.

\* cited by examiner

*Primary Examiner*—Bennett Gelsa
*Assistant Examiner*—Jon D. Epperson
(74) *Attorney, Agent, or Firm*—Merchant & Gould P.C.

(57) ABSTRACT

This invention provides combinatorial chemistry libraries containing thiourea and urea compounds. In addition, the invention relates to methods for constructing combinatorial chemistry libraries containing thiourea and urea compounds. Furthermore, this invention relates to methods for the identification of bioactive thiourea and urea compounds as well as compositions and therapeutic methods for treating cancer.

1 Claim, 5 Drawing Sheets

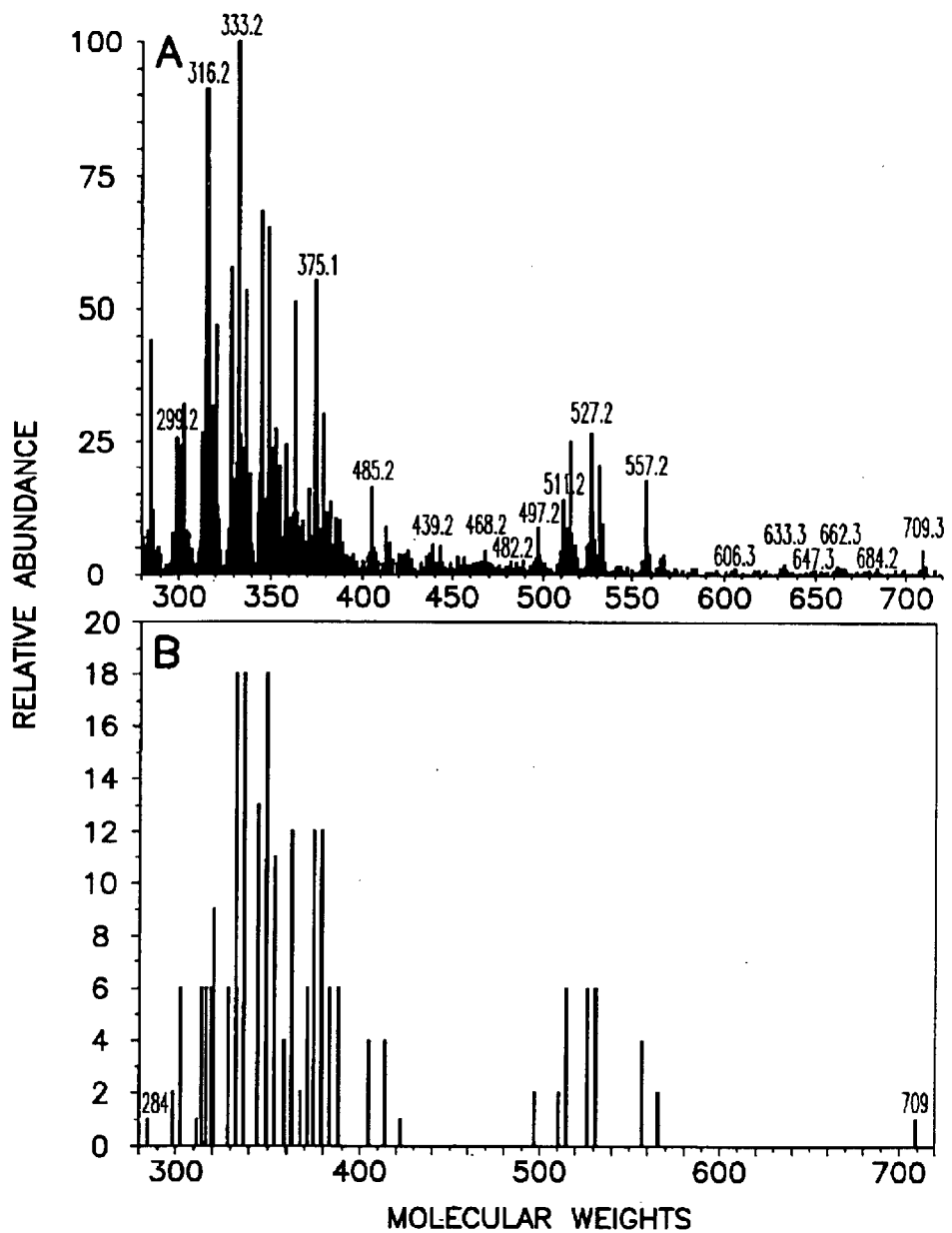
FIGURE 1. FAST ATOMIC BOMBARDMENT (FAB)-MASS SPECTRUM OF COMBINATORIAL CHEMICAL LIBRARY CL1. [A] FAB MS OF CL1. [B] THEORETICAL MASS SPECTRUM OF CL1. THERE ARE 34 DIFFERENT MOLECULAR WEIGHTS IN LIBRARY CL1 BY CALCULATION: 284, 298, 302, 312, 314, 316, 319, 320, 328, 332, 333, 337, 344, 349, 353, 358, 362,367, 371, 374, 379, 383, 388, 404, 413, 422, 497, 511, 515, 527, 531, 557, 566, 709. EVERY EXPECTED MOLECULAR WEIGHT IN CL1 REPRESENTED IN [B] WAS OBSERVED IN THE EXPERIMENTAL MASS SPECTRUM SHOWN IN [A].

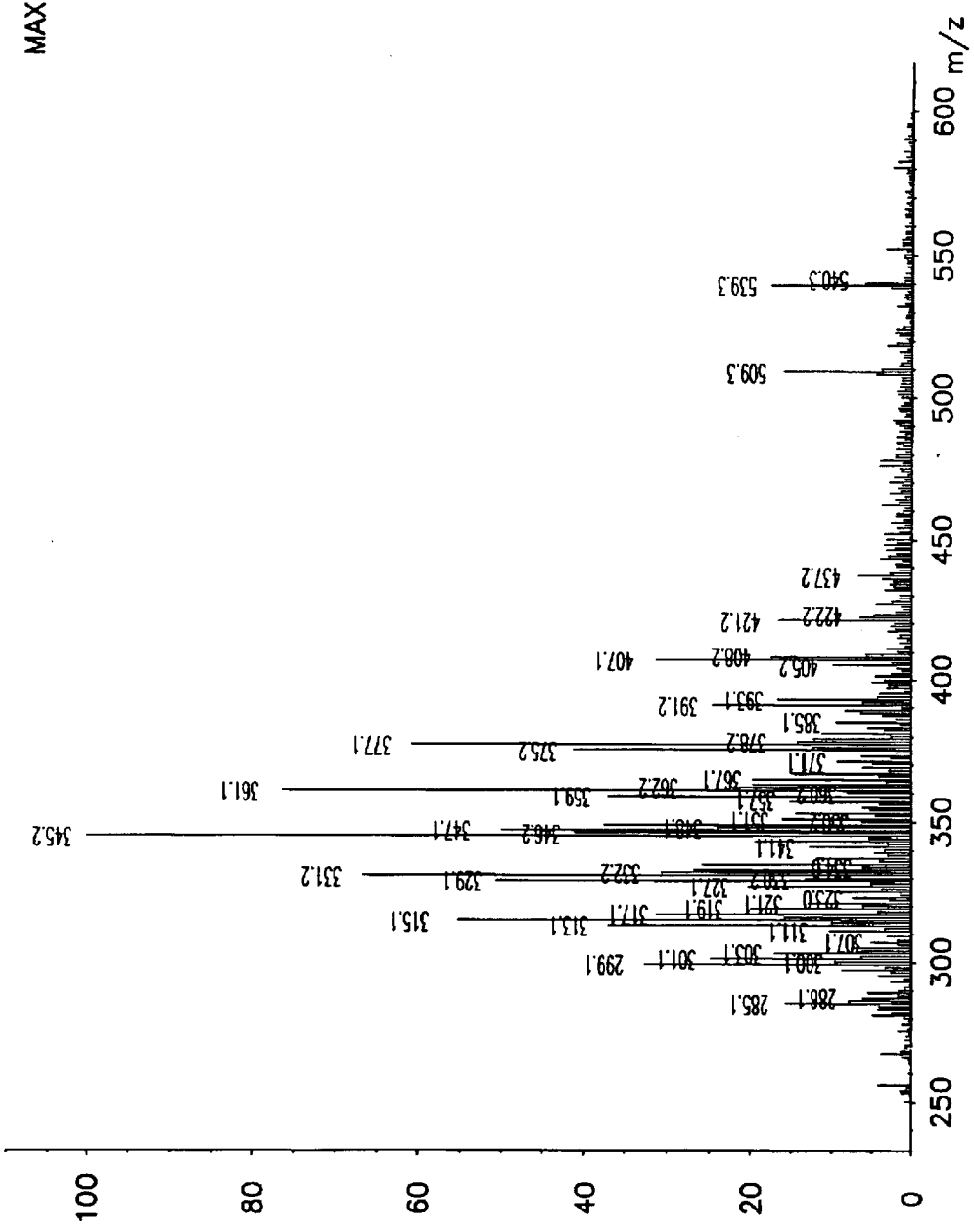

FIG. 3A

```
C:\JOE\DATA\U02.TOF  [A     .00          , #328]
SAMPLE NAME        UREA
PREPARATION        CDC13
MATRIX             CINNAMIC ACID
USER NAME
DEPARTMENT NAME
APPLICATION
COLLECTED          FRI MAY 21 11:57:12 1999
PROCESSED          TUE JUN 01 15:18:34 1999
PRINTED            TUE JUN 01 15:18:55 1999
SEQUENCE
METHOD             C:\HPTOFOLD\METHOD\LOW-POS1.MET*
COLLECTION MODE    AUTO MULTI SHOTS (S/N 61.7) (50 OF 101) MESA 7 [25-25]
LASER ENERGY       1.99 (0.25) UJ    VACUUM      7.59E-007 TORR
MASS RANGE         1000 Da           ION OPTICS  28.0/7.0 KV
MASS FILTER        0 Da              DETECTOR    -4.75 KV
DATA INTERVAL      5.0 NSEC          DIGITIZER   1000 MVFS
POLARITY           POSITIVE          FILTER      NONE
A2 5.2207060 A1 -0.1858900 A0 0.0016550 RES 0.0274605
CALIBRATION - PROGRAM CALCULATED (2-PARAMETER)
CALIBRATION DATA TUE DEC 17 08:29:59 1996
CALIBRATOR SYSTEM OPERATOR
CALIB DATA FILE NEW DATA* [#378]
```

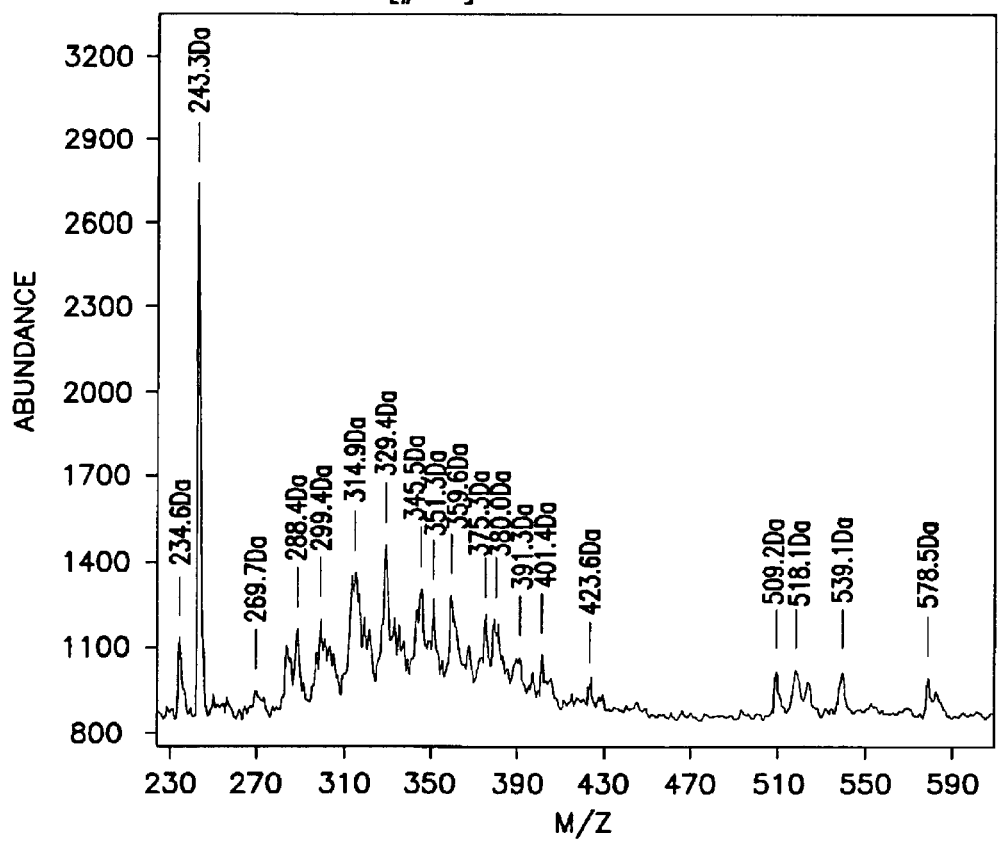

THIOUREA AND UREA LIQUID-PHASE COMBINATORIAL LIBRARIES: SYNTHESIS AND APOPTOSIS INDUCTION

PRIORITY OF THE INVENTION

This application is a continuation application of international application number PCT/US00/06989 filed on Mar. 19, 2000 claiming priority under 35 U.S.C. 119 (a)–(e) to U.S. Provisional Application No. 60/125,146 filed on Mar. 19, 1999; the international application was published under PCT Article 21(2) in English as WO 00/56681.

FIELD OF THE INVENTION

This invention relates to combinatorial chemistry libraries containing thiourea and urea compounds. In addition, the invention relates to methods for constructing combinatorial chemistry libraries containing thiourea and urea compounds. Furthermore, this invention relates to methods for the identification of bioactive thiourea and urea compounds as well as compositions and therapeutic methods for treating cancer.

BACKGROUND OF THE INVENTION

A common method of drug discovery is to first delineate a biochemical pathway that is involved in a targeted pathological process. The biological pathway is analyzed so as to determine crucial elements which, if obstructed, restrained or otherwise adversely modified could inhibit the pathological process. Generally, an assay can be developed that is indicative of the functional ability of an element of the biochemical pathway. The assay can then be performed in the presence of a number of different molecules. The researcher can then determine the molecules that have the desired effect on the pathway, and that molecule or molecules can be used in treatment or can be further modified to augment and enhance the desired effect.

As the assays that are indicative of these pathways become faster, and more easily automated, the rate determining step regarding molecular screening becomes the production of the molecules to be tested. Thus, the development of techniques to rapidly and systematically synthesize large numbers of molecules possessing diverse structural properties has grown in importance. On such technique for rapidly and systematically synthesizing large numbers of molecules possessing diverse structural properties is the construction of combinatorial libraries. Combinatorial chemistry employing solution-phase combinatorial synthesis plays and increasingly important role in drug discovery efforts.

Combinatorial libraries are typically formed via a multi-step synthetic procedure employing either solution-phase or solid-phase methods. The procedure typically includes mixtures of different subunits which are added stepwise to growing oligomers until a desired oligomer size is reached. Alternatively, the subunits can be combined in one synthetic step to produce a random array of oligomers or a combination of the two procedures may be employed. The result is the rapid synthesis of a large, diverse group of chemical compounds that can be screened with the predictive assay developed with regard to the targeted pathological process. Since the chance of finding useful molecules increases with the size of the combinatorial library, it is desirable to generate libraries composed of large numbers of oligomers which vary in their subunit sequence.

Apoptosis is a biochemical process that is an important part of a number of diseases. Apoptosis is a common mode of eukaryotic cell death which is triggered by an inducible cascade of biochemical events leading to activation of endonucleases that cleave the nuclear DNA into oligonucleosome-length fragments. Several of the biochemical events that contribute to apoptotic cell death as well as both positive and negative regulators of apoptosis have recently been identified (Whyllie A., et al. (1980) *Int. Rev. Cytol.* 68, 251–305; Steller H., (1995) *Science* 267, 1445–1449; Fraser, A., Evan, G. (1996) *Cell* 85, 781–784; and Korsmeyer, S. J. (1995). *Trends Genet.* 11, 101–105). Apoptosis plays a pivotal role in the development and maintenance of a functional immune system by ensuring the timely self-destruction of autoreactive immature and mature lymphocytes as well as any emerging target neoplastic cells by cytotoxic T cells.

In addition to the beneficial effects associated with apoptosis, inappropriate apoptosis contributes to the pathogenesis and drug resistance of human leukemias and lymphomas (Cohen, J. J., et al. (1992) *Annu. Rev. Immunol.* 10, 267–293; Linette, G. P., Korsmeyer, S. J. (1994) *Curr. Opin. Cell Biol.* 6, 809–815; and Thompson, C. B. (1995) *Science* 367, 1456–1462). Thus, agents that are useful to modulate apoptosis are potentially useful as therapeutic agents for treating diseases in which inappropriate apoptosis is implicated. As a result, there is a considerable amount of ongoing research devoted to the identification of molecular regulators of apoptosis, and there is currently a need for novel agents (e.g. chemical or biological), and novel therapeutic methods, that are useful for modulating apoptosis. Such agents and methods may be useful for treating cancer (e.g. leukemias and lymphomas) or immune disorders in mammals. They may also be useful as pharmacological tools for use in in vitro or in vivo studies to enhance the understanding of the molecular basis of apoptosis (e.g. the pro-apoptotic versus the anti-apoptotic regulatory signal), as well as the pathogenesis of human lymphoid malignancies.

Novel thiourea and urea compounds have been found to be potent cytotoxic agents with potent activity against cancer cells. For example, certain thiourea and urea compounds exhibit potent cytotoxic activity, particularly against human leukemic cell lines. Additionally, thiourea and urea compounds have been found to be nonnucleoside inhibitors of HIV reverse transcriptase. Currently the production of thiourea and urea compounds however, is limited to the small scale synthesis of individual molecules. Thus, a method for the rapid and systematic synthesis of large numbers of thiourea and urea compounds possessing diverse structural properties is desirable.

SUMMARY OF THE INVENTION

Generally, the present invention relates to a combinatorial library including compounds of the Formula I

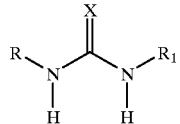

wherein X is S or O;
R and R$_1$ are individually

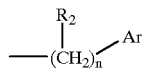

where Ar is aryl; R$_2$ is H or C$_1$ to C$_6$ alkyl; n is 0–3 and where the aryl moiety is optionally substituted from 1 to 7 times with any combination of H, halo, alkyl, haloalkyl, arylalkyl, alkoxy, haloalkoxy, and aralkoxy. One embodiment is a combinatorial library of claim 1, wherein R and R$_1$ are individually

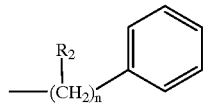

where R$_2$ is H or C$_1$ to C$_6$ alkyl; n is 0–3 and where the phenyl moiety is optionally substituted from 1 to 5 times with any combination of R$_3$ R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, and R$_{27}$; and where R$_3$ is H, R$_4$ is 2-methyl, R$_5$ is 2-trifluoromethyl, R$_6$ is 2-fluoro, R$_7$ 2-chloro, R$_8$ is 2-methoxy, R$_9$ is 2-ethoxy, R$_{10}$ 3-methyl, R$_{11}$ is 3-trifluoromethyl, R$_{12}$ is 3-fluoro, R$_{13}$ is 3-chloro, R$_{14}$ is 3-iodo, R$_{15}$ is 3-methoxy, R$_{16}$ is 4-methyl, R$_{17}$ is 4-trifluoromethyl, R$_{18}$ is 4-fluoro, R$_{19}$ is 4-chloro, R$_{20}$ is 4-bromo, R$_{21}$ is 4-methoxy, R$_{22}$ is 5-trifluoromethyl, R$_{23}$ is 5-fluoro, R$_{24}$ is 6-fluoro, R$_{25}$ is 5-methoxy, R$_{26}$ is 3-benzyloxy, and R$_{27}$ is 4-benzyloxy.

Another embodiment is a method for synthesizing a combinatorial library including compounds of the Formula I:

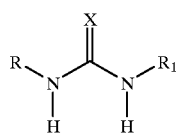

where X is S or O;
R and R$_1$ are individually

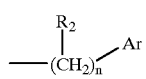

where Ar is aryl; R$_2$ is H or C$_1$ to C$_6$ alkyl; n is 0–3 and where the aryl moiety is optionally substituted from 1 to 7 times with any combination of H, halo, alkyl, haloalkyl, arylalkyl, alkoxy, haloalkoxy, and aralkoxy, including the step of contacting a subunit selected from the group consisting of urea and thiourea with an amine in a suitable carrier.

Yet another embodiment is composition for determining possible apoptosis induction agents for a biological substrate, comprising a combinatorial library or compounds generated therefrom.

A further embodiment of the present invention is a method of killing a cancer cell by contacting the cancer cell with a combinatorial library or compounds generated therefrom.

Another embodiment of the invention includes a kit for determining possible apoptosis induction agents for a biological substrate.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIGS. 1A and B: are FAB mass spectrum of Combinatorial Library 1.

Figure 2B:
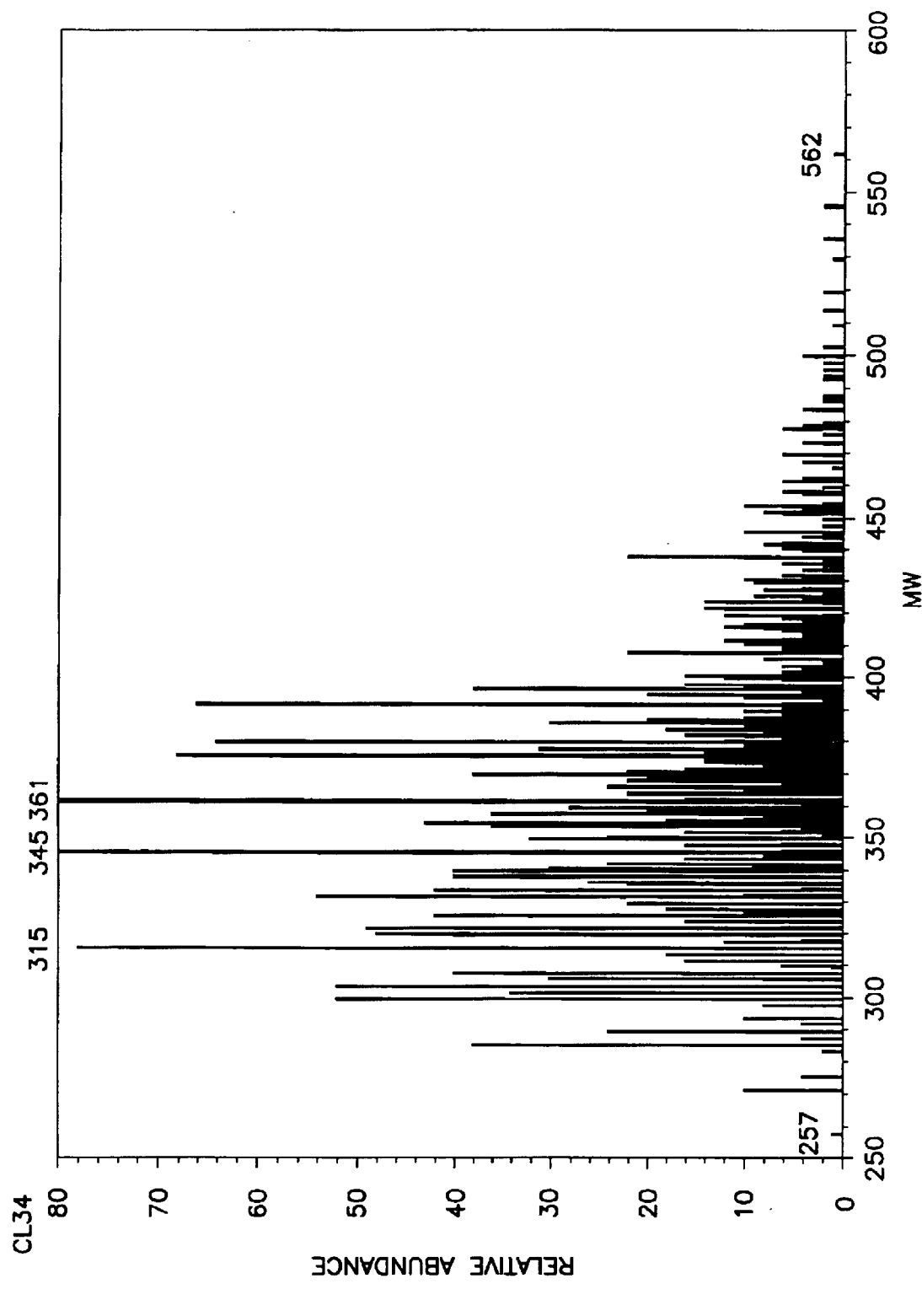
FIGS. 2A and B: are ESI mass spectrum (FIG. 4A) and a computer-generated MS spectrum (FIG. 4B) of Combinatorial Library 34.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE PREFERRED EMBODIMENT

The present invention is believed to be applicable to combinatorial chemistry libraries containing thiourea and urea compounds. In particular, the present invention is directed to combinatorial chemistry libraries containing thiourea and urea compounds, methods for constructing these libraries and methods for the identification of bioactive thiourea and urea compounds. While the present invention is not so limited, an appreciation of various aspects of the invention will be gained through a discussion of the examples provided below.

The term "combinatorial library" refers to an intentionally created collection of differing molecules which can be prepared synthetically and screened for biological activity. A combinatorial library consists of at least two compounds.

The term "combinatorial chemistry" refers to the synthesis of compounds from sets of subunit and chemical reactions used in one or more reaction steps.

The term "alkyl" refers to straight or branched hydrocarbon radicals, such as methyl, ethyl, propyl, butyl, octyl, isopropyl, tert-butyl, sec-pentyl, and the like. Alkyl groups can either be unsubstituted or substituted with one or more substituents, e.g., halogen, alkoxy, aryl, arylalkyl, aralkoxy and the like. Typically, alkyl groups include 1 to 8 carbon atoms, preferably 1 to 5, and more preferably 1 to 3 carbon atoms.

The term "halo" refers to fluoride, chloride, bromide, and iodide radicals.

The term "aryl" refers to monovalent unsaturated aromatic carbocyclic radicals having a single ring, such as phenyl, or multiple condensed rings, such as naphthyl or anthryl, which can be optionally substituted by substituents such as halogen, alkyl, arylalkyl, alkoxy, aralkoxy, and the like.

The term "haloalkyl" refers to an alkyl group substituted with a halo radical as defined above.

The term "alkoxy" refers to an oxygen atom substituted with an alkyl radical as defined above. Typical alkoxy groups include methoxy, ethoxy, propoxy, iopropoxy, and the like. Preferable alkoxy groups include methoxy and ethoxy.

The term "arylalkyl" refers to an alkyl radical defined as above substituted with an aryl radical as defined above. Typical arylalkyl groups include phenethyl, benzyl, and naphthethyl. Preferable alylalkyl groups include phenethyl and benzyl.

The term "aralkoxy" refers to an alkoxy group as defined above where the alkyl group is substituted with an aryl radical as defined above.

The term "haloalkoxy" refers to an alkoxy group as defined above where the alkyl group is substituted with a halo radical as defined above.

The term bioactive refers to a molecule that exhibits anti-cancer, anti-microbial, or anti-viral activity.

Thiourea and Urea Combinatorial Libraries

The present invention provides combinatorial libraries that include thiourea and urea compounds represented by the Formula I:

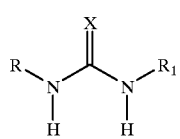

where X is S or O;
R and $R_1$ are individually

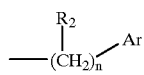

where Ar is aryl; $R_2$ is H or $C_1$ to $C_6$ alkyl; n is 0–3 and where the aryl moiety is optionally substituted from 1 to 7 times with any combination of H, halo, alkyl, haloalkyl, arylalkyl, alkoxy, haloalkoxy, and aralkoxy. In addition, R and $R_1$ include

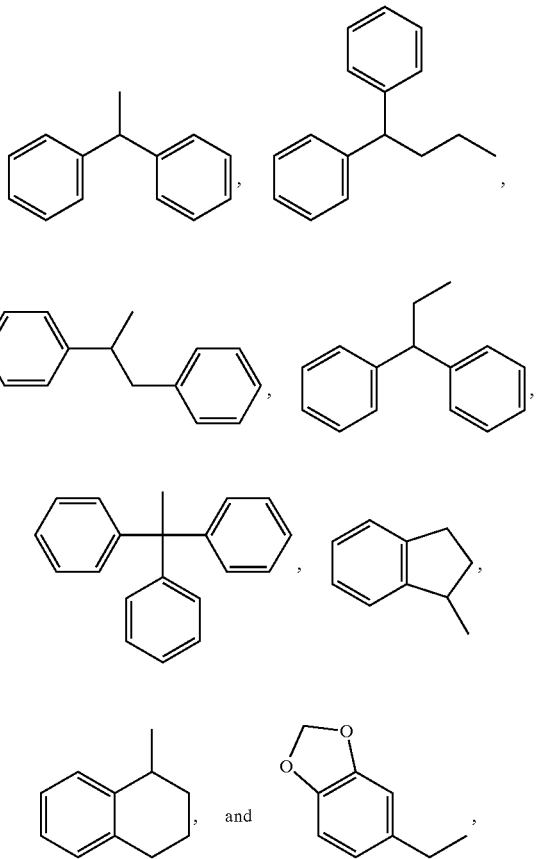

In one embodiment $R_1$ and $R_2$ are individually

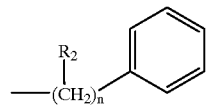

where $R_2$ is H or $C_1$ to $C_6$ alkyl; n is 0–3 and where the phenyl moiety is optionally substituted from 1 to 5 times with any combination of $R_3$ $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$; and where $R_3$ is H, $R_4$ is 2-methyl, $R_5$ is 2-trifluoromethyl, $R_6$ is 2-fluoro, $R_7$ 2-chloro, $R_8$ is 2-methoxy, $R_9$ is 2-ethoxy, $R_{10}$ 3-methyl, $R_{11}$ is 3-trifluoromethyl, $R_{12}$ is 3-fluoro, $R_{13}$ is 3-chloro, $R_{14}$ is 3-iodo, $R_{15}$ is 3-methoxy, $R_{16}$ is 4-methyl, $R_{17}$ is 4-trifluoromethyl, $R_{18}$ is 4-fluoro, $R_{19}$ is 4-chloro, $R_{20}$ is 4-bromo, $R_{21}$ is 4-methoxy, $R_{22}$ is 5-trifluoromethyl, $R_{23}$ is 5-fluoro, $R_{24}$ is 6-fluoro, $R_{25}$ is 5-methoxy, $R_{26}$ is 3-benzyloxy, and $R_{27}$ is 4-benzyloxy.

In a preferred embodiment the combinatorial libraries include compounds of Formula I where $R_1$ and $R_2$ are independently selected from the group

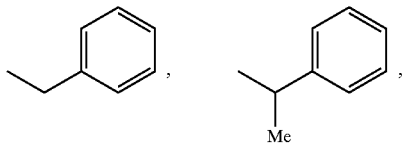

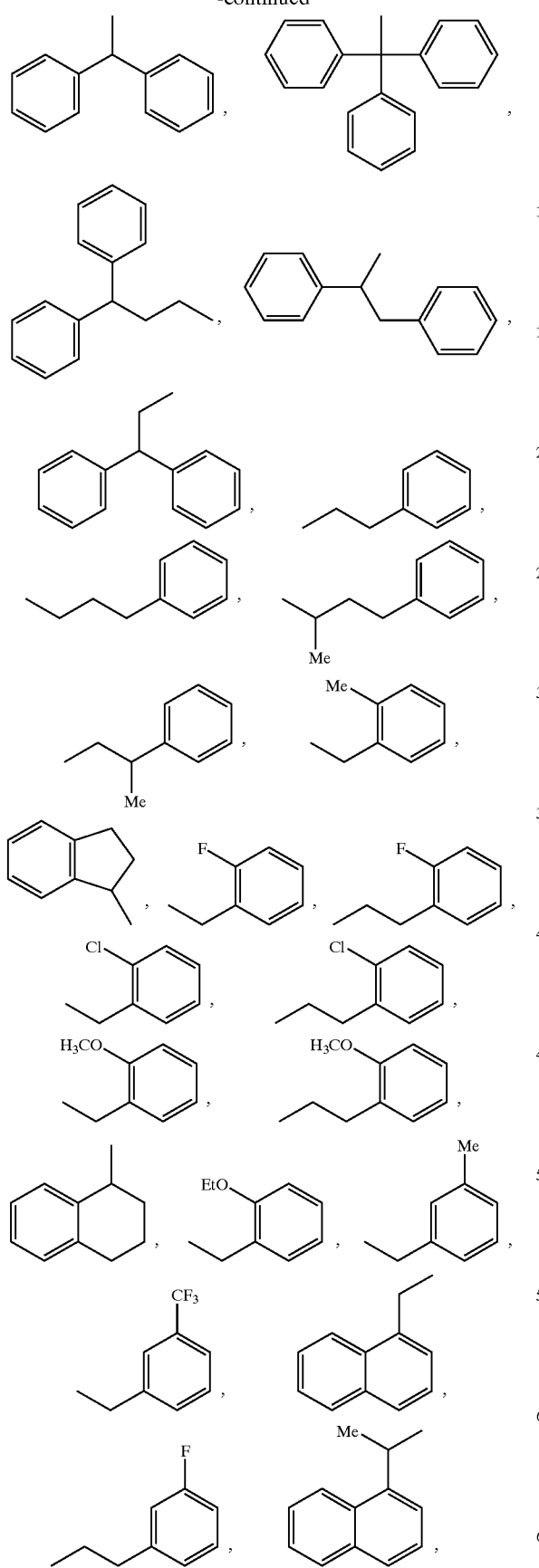
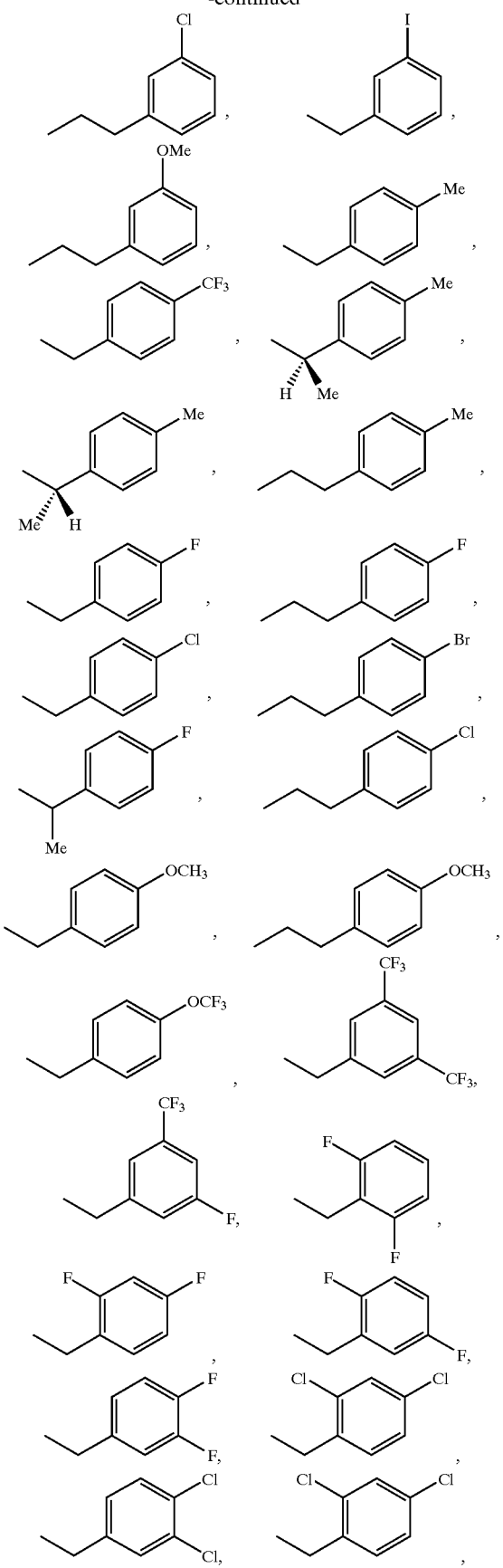

-continued

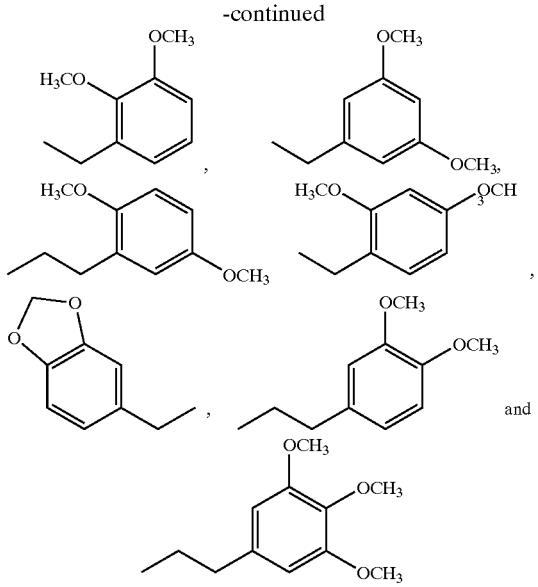

Combinatorial Synthesis

Combinatorial library synthesis is typically performed ether on a solid support, such as peptide synthesis resins, or in liquid phase. For solid support synthesis of combinatorial libraries a large number of beads or particles are suspended in a suitable carrier, such as a solvent, in an initial reaction vessel. The beads, for example, are provided with a functionalized point of attachment for a chemical subunit. The beads are then divided and placed in various separate reaction vessels. The first chemical subunit is attached to the bead, providing a variety of differently substituted solid supports. The beads are washed to remove excess reagents and recombined. The beads are again divided into separate reaction vessels and the second chemical subunit is coupled to the chemical module. This recombining and division synthetic process can be repeated until each of a number of selected chemical subunits have been incorporated onto the molecule attached to the solid support.

Solid-phase synthesis makes it easier to conduct multistep reactions and to drive reactions to completion, because excess reagents can be added and then easily washed away after each reaction step. But a much wider range of organic reactions is available for liquid-phase synthesis, the technology used traditionally by most synthetic organic chemists, and products in solution can be more easily identified and characterized. Liquid phase synthesis of combinatorial libraries typically involves combining all the desired chemical subunits in a suitable carrier, such as a solvent, and applying reactions conditions which facilitate the combining of the various chemical subunits in a random fashion to produce an array of final molecules. Alternatively, the total number of chemical subunits can be split into various grouping. These groupings can be added stepwise to the reaction vessel containing a suitable carrier and another grouping of chemical subunits thereby producing an array of final molecules in a less-random, more systematic and controlled fashion. Thus, the synthesis of compounds of a combinatorial library can take place through several sequential reaction steps in which the same or different sets of subunits and chemical reactions are used, as well as the reaction of multiple subunits in one reaction step to form multicomponent compounds.

Combinatorial library synthesis can be performed either manually or through the use of an automated process. For the manual construction of a combinatorial library, an individual would perform the carious chemical manipulations. For the construction of a combinatorial library through an automated process, the various chemical manipulations will typically be performed robotically.

Combinatorial library synthesis of the present invention is typically performed in liquid phase. The desired chemical subunits (e.g. thioureas, ureas, and amine as defined below) are combined and contacted with each other in a suitable carrier, such as a solvent, at a suitable temperature. Examples of suitable solvents include ethers, such as diethyl ether ($Et_2O$), chlorinated solvents, such as methylene chloride ($CH_2Cl_2$), chloroform, or dichloroethane, aromatics, such as toluene, or acetonitrile. Preferably, the organic solvent is acetonitrile. Suitable reaction temperatures are those which allow the desired reaction to proceed to completion in a minimum amount of time while producing the desired products in high yield and purity. Typically, reaction temperatures are such that the carrier used refluxes. The resulting crude reaction mixture is concentrated, diluted in a suitable solvent, such as a halogenated solvent, washed with an aqueous acid solution and then neutralized. The crude reaction mixture can be concentrated by a variety of methods known to those of skill in the art such as distillation, or evaporation at elevated temperatures or reduced pressure or both. Suitable halogenated solvents used to dilute the concentrated crude reaction mixture include, for example, $CH_2Cl_2$, chloroform, and dichloromethane. Preferable halogenated solvents include chloroform. Aqueous acid solutions useful in the present invention are known to those of skill in the art and include, for example, aqueous solutions of hydrochloric acid or acetic acid. Neutralization agents useful in the present invention are known to those of skill in the art and include, for example, alkaline salts such as CaO, NaOH, KOH and $NaHCO_3$.

The present method typically employs a molar ratio of the various chemical subunits of about 1:1. It shall be understood however, that the molar ratio among the various chemical subunits can be varied to as to affect the final composition of the desired combinatorial library. For example, one subgroup may be added in excess so as to produce a combinatorial library with an excess of compounds which include that particular subgroup.

Typical chemical subunits include ureas and thioureas. Preferable ureas and thioureas include, for example, those that undergo alkylamino, arylamino, and arylalkylamino de-amination. Examples of most preferred ureas and thioureas include 1,1'-thiocarbonyldiimidizole (TCDI), and 1,1'-carbonyldiimidizole (CDI).

Additional chemical subunits include compounds of Formula II

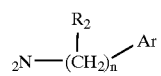

II where Ar is aryl; $R_2$ is H or $C_1$ to $C_6$ alkyl; n is 0–3 and where the aryl moiety is optionally substituted from 1 to 7 times with any combination of H, halo, alkyl, haloalkyl, arylalkyl, alkoxy, haloalkoxy, and aralkoxy. Preferred subunits include compounds of Formula III

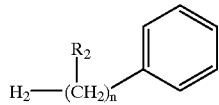

where $R_2$ is H or $C_1$ to $C_6$ alkyl; n is 0–3 and where the phenyl moiety is optionally substituted from 1 to 5 times with any combination of $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, and $R_{27}$; and where $R_3$ is H, $R_4$ is 2-methyl, $R_5$ is 2-trifluoromethyl, $R_6$ is 2-fluoro, $R_7$ 2-chloro, $R_8$ is 2-methoxy, $R_9$ is 2-ethoxy, $R_{10}$ 3-methyl, $R_{11}$ is 3-trifluoromethyl, $R_{12}$ is 3-fluoro, $R_{13}$ is 3-chloro, $R_{14}$ is 3-iodo, $R_{15}$ is 3-methoxy, $R_{16}$ is 4-methyl, $R_{17}$ is 4-trifluoromethyl, $R_{18}$ is 4-fluoro, $R_{19}$ is 4-chloro, $R_{20}$ is 4-bromo, $R_{21}$ is 4-methoxy, $R_{22}$ is 5-trifluoromethyl, $R_{23}$ is 5-fluoro, $R_{24}$ is 6-fluoro, $R_{25}$ is 5-methoxy, $R_{26}$ is 3-benzyloxy, and $R_{27}$ is 4-benzyloxy.

Most preferred subunits include the following compounds

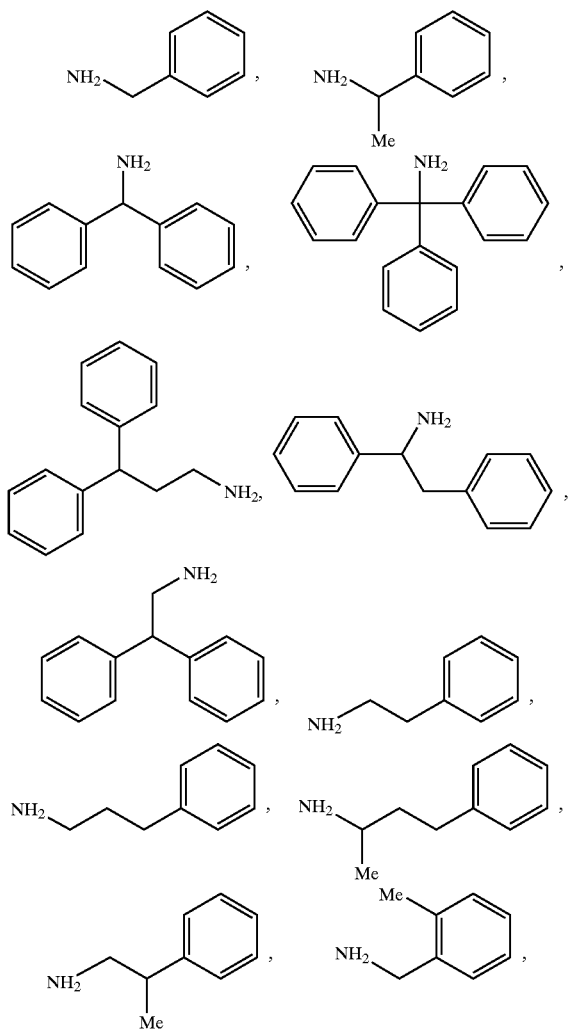

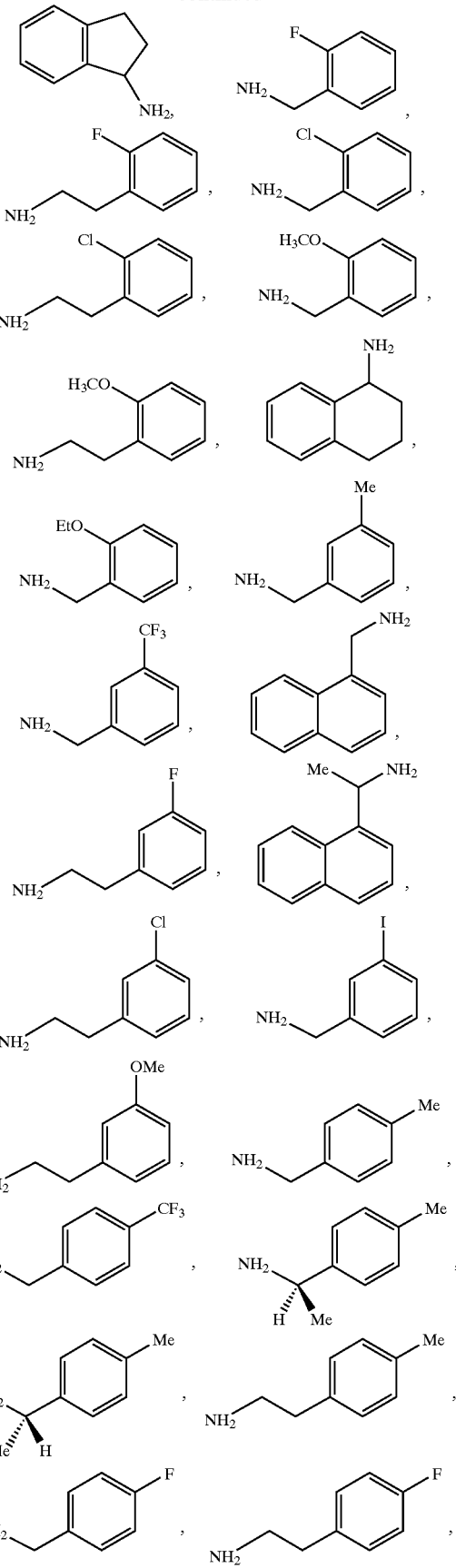

-continued

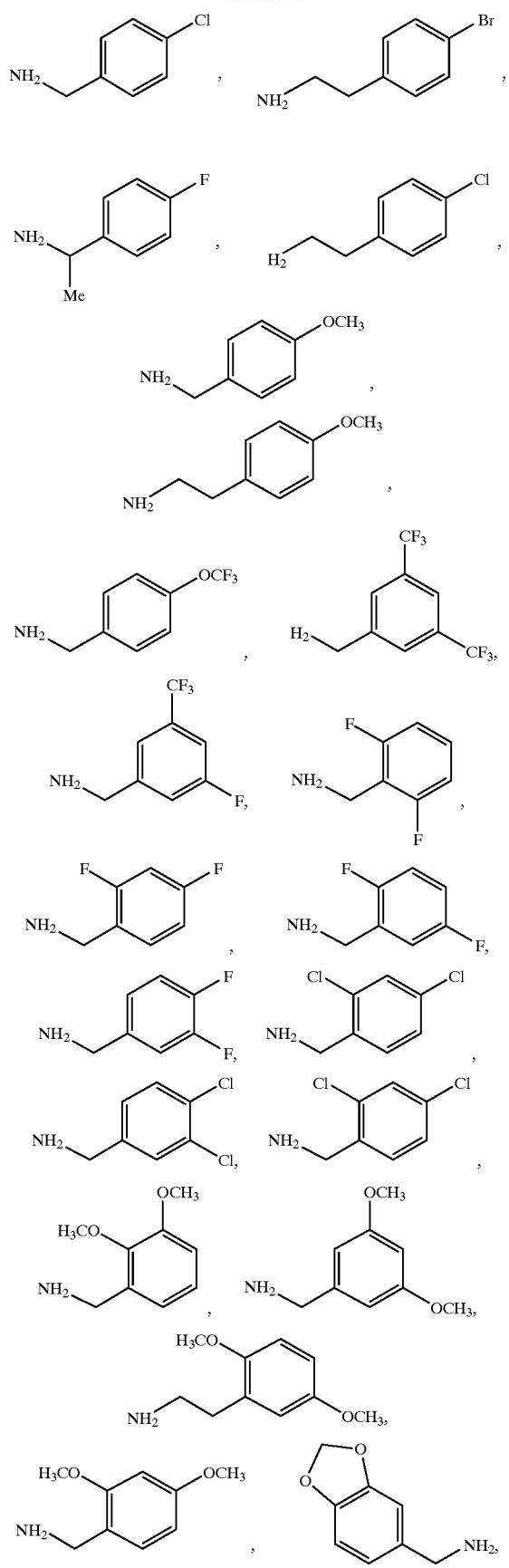

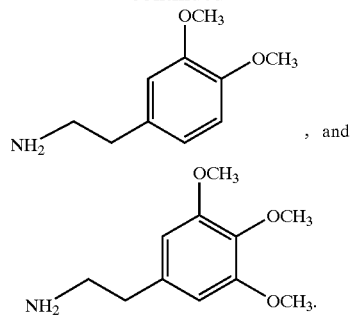

Screening

The present invention is directed toward the generation of thiourea and urea combinatorial libraries. These libraries can be used to select one or more urea or thiourea species that demonstrate biological activity such as, for example, apoptotic activity. Apoptosis plays a pivotal role in the development and maintenance of a functional immune system by ensuring the timely self-destruction of autoreactive immature and mature lymphocytes as well as any emerging target neoplastic cells by cytotoxic T cells. In addition to the beneficial effects associated with apoptosis, inappropriate apoptosis contributes to the pathogenesis and drug resistance of human leukemias and lymphomas.

Several methods have been developed to screen libraries of compounds to identify those compounds having the desired biological activity. Such methods are well known to those of skill in the art. For example, a cellular or enzyme solution may be combined with at solution of the compounds of a particular combinatorial library under conditions favorable to elicit a biological response such as inhibition of an enzyme or regulation of a cellular pathway. The biological activity of library compounds may be detected by any of the numerous biological assays which are well known in the art such as, for example, the MTT (3-[4,5-dimethylthiazol-2-yl]-2,5-diphenyl tetrazolium bromide) assay (Boehringer Mannheim Corp., Indianapolis, Ind.) or the in apoptosis/TUNEL assay (Zhu D et al., Clinical Cancer Research 4:2967–2976, 1998). In cases where the compounds of a given combinatorial library demonstrate biological activity by binding to a biological target such as an enzyme the compound/biological target complex can be separated from other assay components using various methods known to those of skill in the art such as size-exclusion chromatography. The compound/biological target complex can then be denatured to release the compound which can then be isolated using various methods known to those of skill in the art, such as HPLC, and subjected to mass spectrometry for identification.

An alternative manner of identifying biologically active compounds is iterative synthesis and screening to deconvolute the combinatorial library. Iterative synthesis/screeing involves the synthesis of compounds in such a manner that a combinatorial library results that is not directly resolvable to determine the identity of discrete biologically active compounds, but that instead is resolvable to determine the identity of a specific compound in any mixture that shows biological activity when assayed. A new sublibrary is then synthesized based on this information and assayed, and the identity of the next specific subunit determined. The iterative process is continued until the identity of a complete, active molecule is determined. Iterative synthesis/screeing has several characteristics including diminishing library size as the iterations proceed, ending with the last step which involves the synthesis and assaying of the individual compound. Various methods of deconvolution fall within the iteration definition and will be considered as a form of iterative synthesis/screening.

EXAMPLES

Example 1

Synthesis of N,N'-Bis(2-phenylethyl)thiourea Combinatorial Libraries, Deconvolution and Identification of Biologically Active Species The reaction is accomplished by phenethylamine substitution of imidazoles in thiocarbonyldiimidazole (TCDI) in solvent acetonitrile under reflux. The reaction is carried out in equimolar ratio. After the reaction is completed, the substituted imidazole is protonated with dilute aqueous acid and separated during solvent/solvent extraction.

Stage (I): synthesis of compound 1 in Scheme 1.

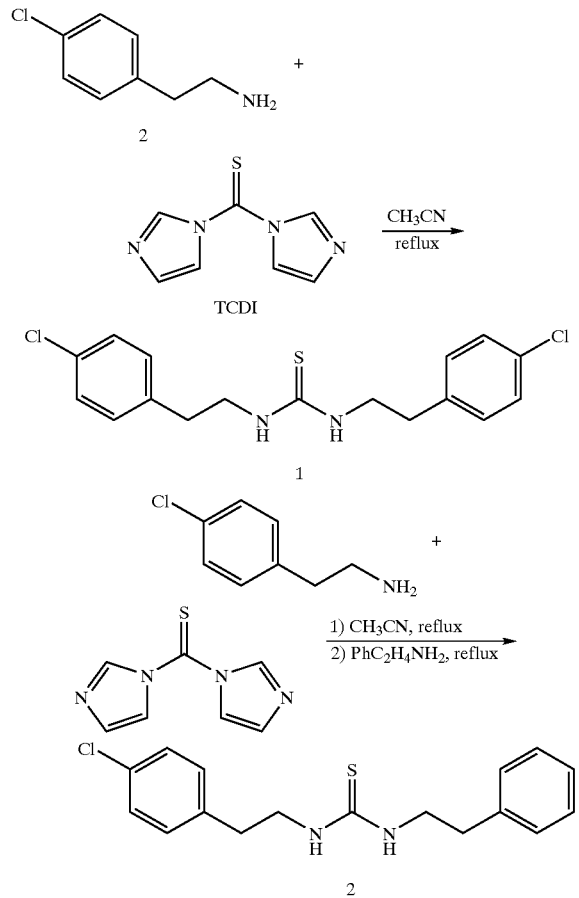

The synthesis of compound 1 was carried out by adding an equimolar amount of p-chlorophenethylamine into a solution of TCDI in acetonitrile at 0° C., followed by reflux for 1 h. Thin-layer chromatography (TLC) indicated the completion of the reaction. The concentrated reaction mixture was re-dissolved in $CHCl_3$. The substituted imidazole from TCDI was washed out with dilute hydrochloric acid (0.65 M) during liquid/liquid extraction. After neutralization (saturated $NaHCO_3$ solution), drying ($MgSO_4$) and concentration; a white powder (m.p. 126° C.) was obtained as the desired product (1) with 90% yield and 99% purity by HPLC.

The structure of compound 1 was confirmed with $^1$H NMR, $^{13}$C NMR, MALDI-TOF MS, and elemental analysis:

1,3-Bis(p-chlorophenethyl)-2-thiourea (compound 1). $^1$H NMR (300 MHz, $CDCl_3$, TMS) d 7.28 (d, $^3J(H,H)$=8.4 Hz, 4H, Ar), 7.11 (d, $^3J(H,H)$=8.4 Hz, 4H, Ar), 5.58 (bs, 2H, NH), 3.62 (bs, 4H, α-$CH_2$), 2.84 (t, $^3J(H,H)$=6.9 Hz, 4H, β-$CH_2$); $^{13}$C NMR d 181.6, 136.6, 132.4, 130.0, 128.7, 45.2, 34.4; MS: m/z (MALDI-TOF) 353.3 ($C_{17}H_{18}Cl_2N_2S$ requires 353.3); UV/Vis ($CH_3CN$) $1_{max}$ 194, 224, and 249 nm; HPLC retention time 15.9 min with the following conditions: HP 1100 Series with a LiChrospher 100 RP-18 (5 mm) column (Part #79925OD-584, 250–4), mobile phase: water/acetonitrile=50/50, flow rate: 1.5 mL/min, injection volume: 30 mL, wavelength: 225 nm. Anal. Calcd for C, 57.79; H, 5.13; Cl, 20.07; N, 7.93; S, 9.07. Found: C, 57.90; H, 5.13; Cl, 20.02; N, 7.88; S, 9.03.

A two-step one-pot procedure was also developed to substitute one imidazole on TCDI for each step. First, one molar equivalent of p-chlorophenethylamine was allowed to react with TCDI under 0° C. followed by reflux for 1 h. The mono-substituted thiocarbonyl intermediate was less polar as indicated by TLC ($R_f$ 0.76) vs. the di-substituted compound 2 ($R_f$ 0.46). After the completion of the first substitution by p-chlorophenethylamine, one molar equivalent of phenethylamine was added at the room temperature, followed by reflux for 1 h. After work-up, a yellow wax was obtained as product with a quantitative yield.

The structure of compound 2 was confirmed with $^1$H NMR, $^{13}$C NMR, MALDI-TOF MS and elemental analysis:

1-(p-Chlorophenethyl)-3-phenethyl-2-thiourea (Compound 2). $^1$H NMR (300 MHz, $CDCl_3$, TMS) d 7.33–7.09 (m, 9H, Ar), 5.62 and 5.55 (2 bs, 2H, NH), 3.62 (bs, 4H, α-$CH_2$), 2.87 (t, $^3J(H,H)$=6.9 Hz, 2H, β-$CH_2$), 2.83 (t, $^3J(H,H)$=6.6 Hz, 2H, b-$CH_2$); $^{13}$C NMR d 181.5, 138.1, 136.7, 132.3, 130.0, 128.7, 128.6, 126.6, 45.3, 35.0, 34.4; MS: m/z (MALDI-TOF) 320.5 ($C_{17}H_{19}ClN_2S$ requires 318.9); UV/Vis $1_{max}$ 192, 212 (shoulder), and 249 nm; HPLC retention time 10.3 min. Anal. Calcd for $C_{17}H_{19}ClN_2S$: C, 64.04; H, 6.01; Cl, 11.12; N, 8.79; S, 10.06. Found: C, 64.00; H, 6.07; Cl, 11.00; N, 8.87; S, 10.11.

Stage (II): synthesis of a small mixture library (SML) containing only three members (1, 2 and 3 in Scheme 2) as a model, starting from an equimolar mixture of phenethylamine and p-chlorophenethylamine in acetonitrile. The same procedure was followed as in stage (I). The library was obtained as a white powder with a quantitative yield.

Scheme 2
Synthesis of a small mixture library (SML)

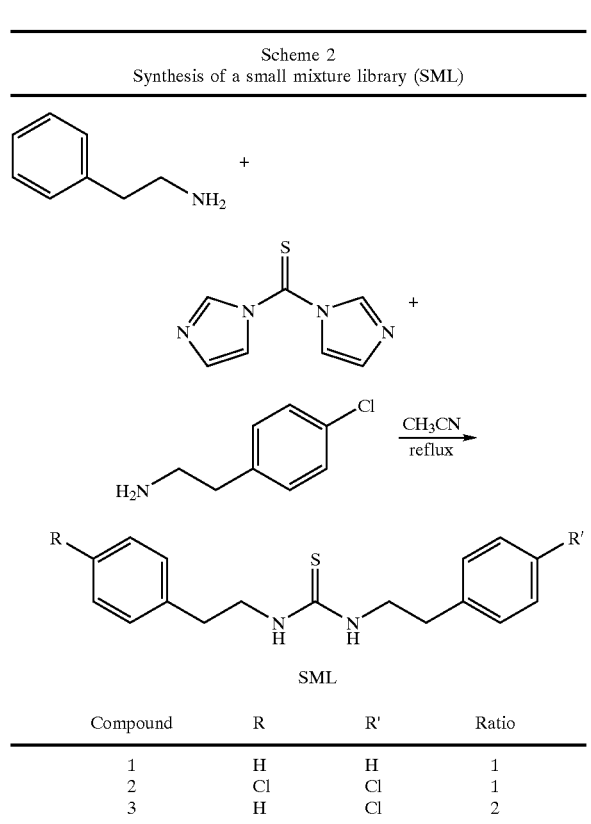

| Compound | R | R' | Ratio |
|---|---|---|---|
| 1 | H | H | 1 |
| 2 | Cl | Cl | 1 |
| 3 | H | Cl | 2 |

The composition of SML was confirmed with $^1$H NMR, LC-MS and elemental analysis:

SML. $^1$H NMR (300 MHz, CDCl$_3$, TMS) d 7.35–7.08 (m, 9H, Ar), 5.62 (bs, 2H, NH), 3.62 (bs, 4H, α-CH$_2$), 2.84 (quintet, 4H, β-CH$_2$). LC-MS retention time 7.4 min corresponds to m/z 285.0 Da, 9.4 min to 319.0 Da, and 12.2 min to 353.0 Da; calcd mass of 284.4 (3), 318.9 (2) and 353.3 (1). Anal. Calcd for 1/2/3=1/2/1: C, 64.42; H, 6.05; Cl, 10.58; N, 8.84; S, 10.11. Found: C, 64.06; H, 6.02; Cl, 11.10; N, 8.84; S, 10.08.

Stage (III), a main library (CL1) was synthesized (Chart 1) utilizing the same method as that given in Stage II above, and started with an equimolar solution of 15 amines. The number of members in a combinatorial library can be predicted based on the following formula that takes into account the number of differing substituents, and the number of possible positions.

Number of members in library=n+C(n,r)
=n+n!/[(n−r)! X r!]
Number of members in library=15+15!/[(15−2)!×2!]= 120.

The main library, CL1, that was synthesized had 15 possible substituents at two different possible positions, leading to 120 members in the combinatorial library.

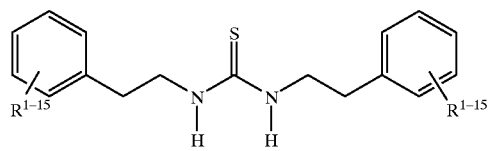

$R^{1-15}$=H; 4-Me; 2-F; 3-F; 4-F; 2-MeO; 3-MeO; 4-MeO; 2-Cl; 3-Cl; 4-Cl; 2,5-(MeO)$_2$; 3,4-(MeO)$_2$; 2,4-Cl$_2$; 3,4-(BnO)$_2$

Chart 1. CL1 (120 Members)

The composition of CL1 was confirmed with $^1$H NMR and MS:

CL1. $^1$H NMR (300 MHz, CDCl$_3$, TMS) d 7.42–6.70 (m, rel. intensity 16, Ar), 5.75 (br, rel. intensity 3.5, NH), 5.12 (2 peaks, rel. intensity 1, OCH$_2$-Ph), 3.86–3.61 (m, rel. intensity 15, a-CH$_2$ and OCH$_3$), 2.84 (m, rel. intensity 10, b-CH$_2$), 2.32 (s, rel. intensity 1, CH$_3$-Ph).

FIG. 1A shows the FAB MS spectrum of CL1. The mass range 284–709 corresponds to the 34 different molecular weights out of 120 members in CL1. To assist visual comparison, a theoretical mass spectrum of CL1 was generated manually with a DeltaGraph Program (FIG. 1B, which displays primary peaks only (isotopes not considered.). The mass distribution can generally be viewed as three groups: 284–422, 497–566, and 709. The FAB MS in FIG. 1A matches the theoretical mass spectrum profile in FIG. 1B.

Stage (4): deconvolution and re-synthesis were guided by an iterative screening procedure during which the cytotoxic anti-cancer activities of the individual sub-libraries were measured against the human leukemia cell lines NALM-6 and MOLT-3 using MTT assays. In general, whenever feasible, an active library was evenly splitted into two sub-libraries and upon biologic testing the more active one of the two sub-libraries was selected for further iteration. However, this is not always true when even-splitting was not possible or some special consideration. For example, library CL1 was discovered to be active and was primarily split to two uneven libraries (CL3 with 55 members, and CL4 with 64 members, Chart 2 and Chart 3). Another special example is the small 10-member sublibrary CL2. Since fluorinated compounds may possess enhanced activities and since fluorine has similar atomic radius with hydrogen, CL2 (10 members, Chart 2) was constructed with fluorine-substituted phenethylamines and phenethylamine.

Chart 2. Libraries CL2–12.

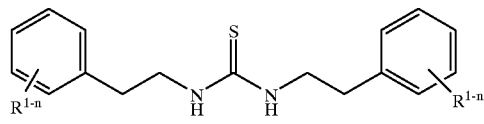

CL2 (10 Members)
$R^{1-4}$=H, 2-F, 3-F, 4-F.

CL3 (55 Members)
$R^{1-10}$=4-Me; 2-F; 4-F; 2-MeO; 4-MeO; 2-Cl; 4-Cl; 2,5-(MeO)$_2$; 2,4-Cl$_2$; 3,4-(BnO)$_2$.

CL5 (28 Members)

$R^{1-7}$=4-Me; 2-F; 4-F; 2-MeO; 4-MeO; 2-Cl; 4-Cl.

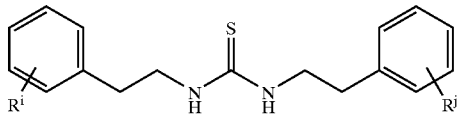

CL4 (64 Members)

$R^i$=H; 3-F; 3-MeO; 3-Cl; 3,4-(MeO)$_2$.

$R^j$=4-Me; 2-F; 3-F; 4-F; 2-MeO; 3-MeO; 4-MeO; 2-Cl; 3-Cl; 4-Cl; 2,5-(MeO)$_2$; 3,4-(MeO)$_2$; 2,4-Cl$_2$; 3,4-(BnO)$_2$.

CL6 (27 Members)

$R^i$=2,5-(MeO)$_2$; 2,4-Cl$_2$; 3,4-(BnO)$_2$.

$R^j$=4-Me; 2-F; 4-F; 2-MeO; 4-MeO; 2-Cl; 4-Cl; 2,5-(MeO)$_2$; 2,4-Cl$_2$; 3,4-(BnO)$_2$.

CL7 (15 Members)

$R^i$=2,5-(MeO)$_2$; 2,4-Cl$_2$; 3,4-(BnO)$_2$.

$R^j$=2-F; 4-F; 2-Cl; 4-Cl; 2,4-Cl$_2$.

CL8 (14 Members)

$R^i$=2,5-(MeO)$_2$; 2,4-Cl$_2$; 3,4-(BnO)$_2$ $R^j$=4-Me; 2-MeO; 4-MeO; 2,5-(MeO)$_2$; 3,4-(BnO)$_2$.

CL9 (6 Members)

$R^i$=2,5-(MeO)$_2$; 2,4-Cl$_2$; 3,4-(BnO)$_2$.

$R^j$=2-F; 2-Cl.

CL10 (6 Members)

$R^i$=2,5-(MeO)$_2$; 2,4-Cl$_2$; 3,4-(BnO)$_2$.

$R^j$=4-F, 4-Cl.

CL11 (6 Members)

$R^i$=2,5-(MeO)$_2$; 2,4-Cl$_2$; 3,4-(BnO)$_2$.

$R^j$=4-Me; 4-MeO.

CL12 (8 Members)

$R^i$=2,5-(MeO)$_2$; 2,4-Cl$_2$; 3,4-(BnO)$_2$.

$R^j$=2-MeO. 2,5-(MeO)$_2$; 3,4-(BnO)$_2$.

Chart 3. A flow chart of deconvolution. The numbers in parentheses under each designated library represent the MTT assay IC$_{50}$ values (in μg/ml) against NALM-6 and MOLT-3 human leukemia cells, respectively.

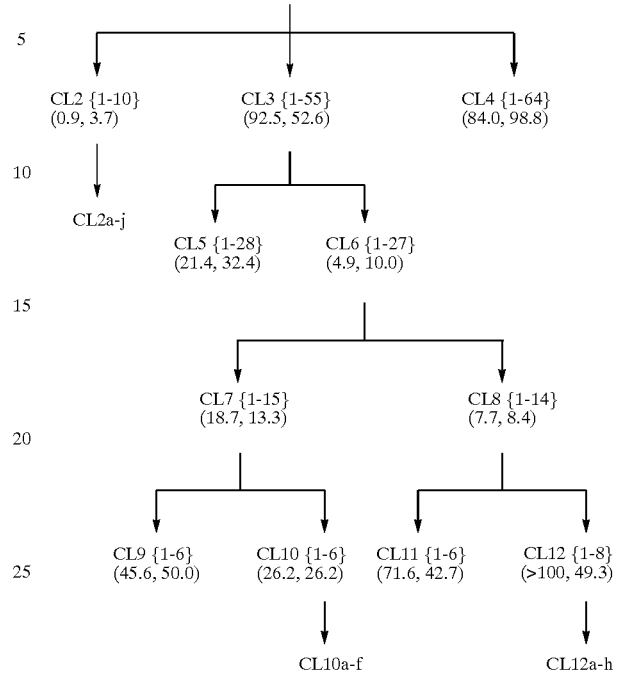

CL2 is significantly more potent than CL3 and CL4. However, at this stage, we could not exclude the possibility that dilution in CL3 and CL4 played a function since they contain more members. Thus, one of these two sublibraries, CL3, was split to CL5 (28 members) and CL6 (27 members, Chart 4). CL6 displayed higher potency, being split to CL7 (15 members) and CL8 (14 members, two members were overlapping in CL7 and CL8). Library CL8 is more active in the MTT assay, it was split to CL11 (6 members) and CL12 (8 members). The eight members in CL12 were synthesized individually. At this stage, since the difference between CL8 and CL7 was not significant, CL7 was also split to CL9 and CL10. And the members of CL10 were synthesized individually. The splitting process is summarized in Chart 3. The activity data are shown in Table 1. The most active CL10 compound was CL10b. The most active CL12 compounds were CL12a and CL12b.

TABLE 1

Structure and Activity of Libraries CL2, CL10 and CL12.

| Structure | $R^i$ | $R^j$ | MW | IC$_{50}$ Nalm6 | (MTT) Molt3 |
|---|---|---|---|---|---|
| CL1 | | | | 13.1 | 37.7 |
| CL2 | | | | 0.9 | 3.7 |
| CL2a | H | H | 284.4 | 18.2 | 17.4 |
| CL2b | H | 2-F | 302.4 | 21.3 | 21.1 |
| CL2c | H | 3-F | 302.4 | 17.6 | 12.1 |
| CL2d | H | 4-F | 302.4 | 17.5 | 13.8 |
| CL2e | 2-F | 2-F | 320.4 | 19.8 | 19.8 |
| CL2f | 2-F | 3-F | 320.4 | 17.0 | 13.0 |
| CL2g | 2-F | 4-F | 320.4 | 13.9 | 11.2 |
| CL2h | 3-F | 3-F | 320.4 | 14.7 | 12.7 |
| CL2i | 3-F | 4-F | 320.4 | 18.2 | 12.9 |
| CL2j | 4-F | 4-F | 320.4 | unstable | compound |
| CL3 | | | | 92.5 | 52.6 |

TABLE 1-continued

Structure and Activity of Libraries CL2, CL10 and CL12.

| Structure | $R^i$ | $R^j$ | MW | $IC_{50}$ Nalm6 | (MTT) Molt3 |
|---|---|---|---|---|---|
| CM |  |  |  | 84.0 | 98.8 |
| CL5 |  |  |  | 21.4 | 32.4 |
| CL6 |  |  |  | 4.9 | 10.0 |
| CL7 |  |  |  | 18.7 | 13.3 |
| CL8 |  |  |  | 7.7 | 8.4 |
| CL9 |  |  |  | 45.6 | 50.0 |
| CL10 |  |  |  | 26.2 | 26.2 |
| CL10a | 4-F | 2,5-(MeO)$_2$ | 362.5 | 29.2 | 28.5 |
| CL10b | 4-F | 2,4-Cl$_2$ | 371.3 | 14.8 | 26.3 |
| CL10c | 4-Cl$_2$ | 2,5-(MeO)$_2$ | 378.9 | 33.6 | 29.0 |
| CL10d | 4-Cl | 2,4-Cl$_2$ | 487.8 | 22.0 | 29.7 |
| CL10e | 4-F | 3,4-(BnO)$_2$ | 514.7 | >100 | >51.4 |
| CL10f | 4-Cl | 3,4-(BnO)$_2$ | 531.1 | >100 | >100 |
| CL11 |  |  |  | 71.6 | 42.7 |
| CL12a | 2-MeO | 2,5-(MeO)$_2$ | 374.5 | 17.4 | 10.9 |
| CL12b | 2-MeO | 2,4-Cl$_2$ | 383.3 | 17.1 | 11.6 |
| CL12c | 2,5-(MeO)$_2$ | 2,5-(MeO)$_2$ | 404.5 | 28.9 | 39.8 |
| CL12d | 2,5-(MeO)$_2$ | 2,4-Cl$_2$ | 413.4 | 40.9 | 34.1 |
| CL12e | 2-MeO | 3,4-(BnO)$_2$ | 526.7 | 58.1 | 76.7 |
| CL12F | 2,5-(MeO)$_2$ | 3,4-(BnO)$_2$ | 556.7 | 27.4 | 37.2 |
| CL12g | 2,4-Cl$_2$ | 3,4-(BnO)$_2$ | 565.6 | >100 | 21.8 |
| CL12h | 3,4-(BnO)$_2$ | 3,4-(BnO)$_2$ | 708.9 | 47.8 | 73.3 |

Cytotoxic Activity Assay

The cytotoxic activity of the CL2 library compounds was investigated via apoptosis/TUNEL assay. TUNEL assay allows the detection of exposed 3'hydroxyl groups in fragmented DNA. The CL2 compounds prepared as described above, were tested, along with DMSO as a control.

The cytotoxicity assay of various CL2 compounds against human tumor cell lines was performed using the MTT (3-[4,5-dimethylthiazol-2-yl]-2,5-diphenyl tetrazolium bromide) assay (Boehringer Mannheim Corp., Indianapolis, Ind.). Briefly, exponentially growing tumor cells were seeded into a 96-well plate at a density of 2.5×10$^4$ cells/well and incubated for 36 hours at 37° C. prior to compound exposure. On the day of treatment, culture medium was carefully aspirated from the wells and replaced with fresh medium containing the CL2 compounds at concentrations ranging from 0.0 to 100 µM. Triplicate wells were used for each treatment.

Human cell lines were obtained from American Type Culture Collection (Rockville, Md.) and maintained as a continuous cell line in Dulbecco's modified Eagles' medium supplemented with 10% fetal bovine serum and antibiotics. Cells used in this study include human leukemia cells (NALM-6 and MOLT-3).

The cells were incubated with the various compounds for 24–36 hours at 37° C. in a humidified 5% CO$_2$ atmosphere. To each well, 10 µl of MTT (0.5 mg/ml final concentration) was added and the plates were incubated at 37° C. for 4 hours to allow MTT to form formazan crystals by reacting with metabolically active cells. The formazan crystals were solubilized overnight at 37° C. in a solution containing 10% SDS in 0.01 M HCl. The absorbance of each well was measured in a microplate reader (Labsystems) at 540 nm and a reference wavelength of 690 nm. To translate the OD$_{540}$ values into the number of live cells in each well, the OD$_{540}$ values were compared to those on standard OD$_{540}$-versus-cell number curves generated for each cell line. The percent survival was calculated using the formula:

$$\% \text{ Survival} = \frac{\text{live cell number [test]}}{\text{live cell number [control]}} \times 100$$

The IC$_{50}$ values were calculated by non-linear regression analysis.

The demonstration of apoptosis was performed by the in situ nick-end-labeling method using ApopTag in situ detection kit (Oncor, Gaithersburg, Md.) according to the manufacturer's recommendations. Exponentially growing cells were seeded in 6-well tissue culture plates at a density of 50×10$^4$ cells/well and cultured for 36 hours at 37° C. in a humidified 5% CO$_2$ atmosphere. The supernatant culture medium was carefully aspirated and replaced with fresh medium containing unconjugated EGF or EGF-P154 at a concentration of 10, 25, or 50 Tg/ml. After a 36 hour incubation at 37° C. in a humidified 5% CO$_2$ incubator, the supernatants were carefully aspirated and the cells were treated for 1–2 minutes with 0.1% trypsin. The detached cells were collected into a 15 ml centrifuge tube, washed with medium and pelleted by centrifugation at 1000 rpm for 5 minutes. Cells were resuspended in 50 Tl of PBS, transferred to poly-L-lysine coated coverslips and allowed to attach for 15 minutes. The cells were washed once with PBS and incubated with equilibration buffer for 10 minutes at room temperature.

After removal of the equilibration buffer, cells were incubated for 1 hour at 37° C. with the reaction mixture containing terminal deoxynucleotidyl transferase (TdT) and digoxigenin-11-UTP for labeling of exposed 3'-hydroxyl ends of fragmented nuclear DNA. The cells were washed with PBS and incubated with anti-digoxigenin antibody conjugated to FITC for 1 hour at room temperature to detect the incorporated dUTP. After washing the cells with PBS, the coverslips were mounted onto slides with Vectashield containing propidium iodide (Vector Labs, Burlingame, Calif.) and viewed with a confocal laser scanning microscope. Non-apoptotic cells do not incorporate significant amounts of dUTP due to lack of exposed 3-hydroxyl ends, and consequently have much less fluorescence than apoptotic cells which have an abundance of exposed 3'-hydroxyl ends. In control reactions, the TdT enzyme was omitted from the reaction mixture.

The cytotoxic activities of CL1 and CL3 library compounds were also investigated via apoptosis/TUNEL assay described above. Combinatorial libraries 1, 2, and 3 all caused apoptosis of NALM-6 leukemia cells in a concentration-dependent fashion.

Example 2

Synthesis of Combinatorial Thiourea Mixture Libraries In Solution Phase

A mixture containing 1830 components was synthesized in solution phase in one step from thiocarbonyldiimidazole and 60 commercially-available amines. Subsequently, 60 positional scanning deconvolution libraries were synthesized for the identification of the active components. Several individual compounds were synthesized and tested for biologic activity. Among them, 1,3-bis(1,2-diphenylethyl)-2-thiourea and 1-(1,2-diphenylethyl)-3-(diphenylmethyl)-2-thiourea are the most potent with $IC_{50}$ values below 10 μg/ml in MTT assays.

Scheme 3

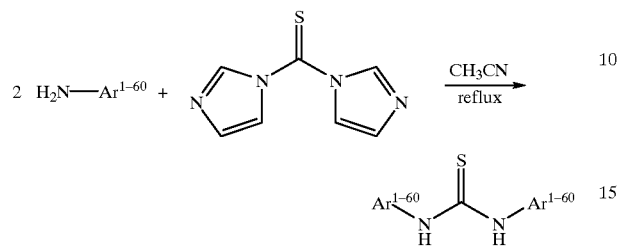

The parent library containing 1830 members was assembled in one synthetic step using Scheme 3. The number of the members in CL34 is calculated as: 60+C(60, 2)=60+60!/(2×58!)=60+60×59/2=1830.

A mixture of equimolar 60 amines (Table 2) substituted the imidazole moiety in TCDI under reflux. Specifically, a solution of 60 amines (1 mmol each, Table 2) in acetonitrile (60 mL) was added into a solution of TCDI (5.35 g, 30 mmol) in acetonitrile (100 mL) dropwise at 0° C., followed by reflux for 1 h. The completion of the reaction was monitored with TLC. The same work-up was followed as described in Example 1. A yellow gel was obtained as the desired library in 70% yield. $^1$H NMR included all peaks observable with the individual compound and SML.

TABLE 2

The 60 building blocks used to assemble the parent library.

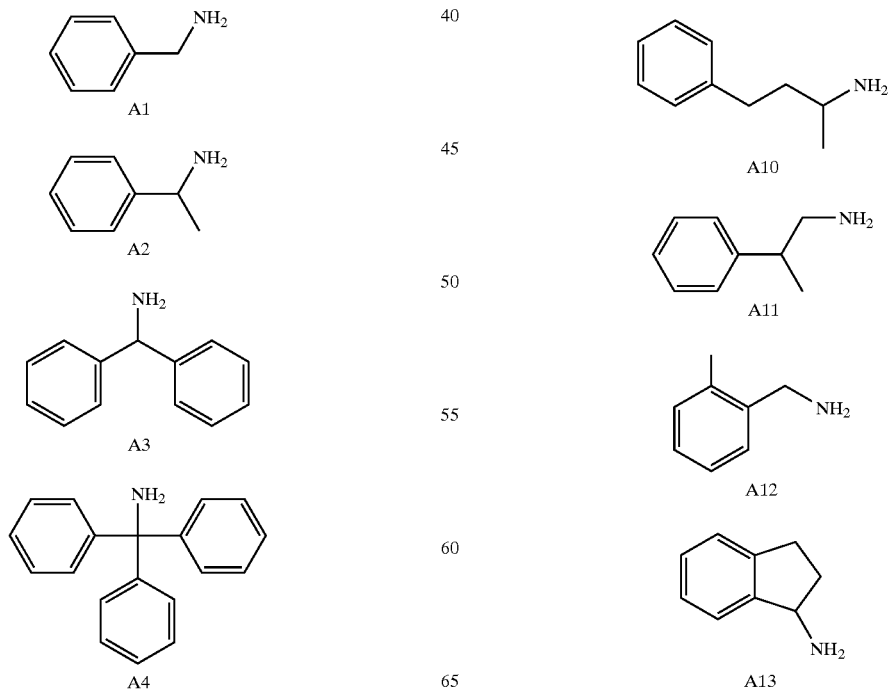

TABLE 2-continued

The 60 building blocks used to assemble the parent library.

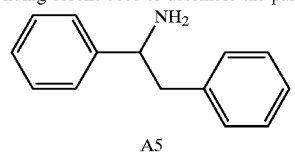

A5

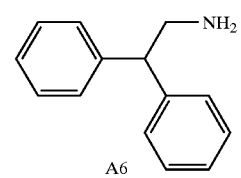

A6

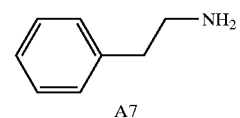

A7

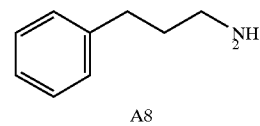

A8

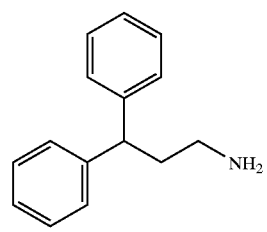

A9

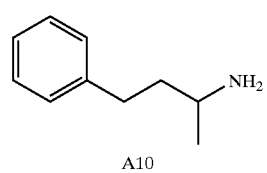

A10

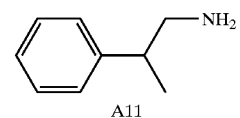

A11

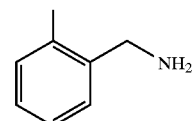

A12

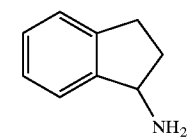

A13

TABLE 2-continued
The 60 building blocks used to assemble the parent library.
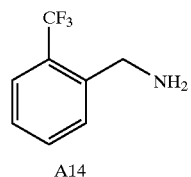
A14
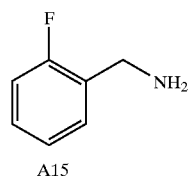
A15
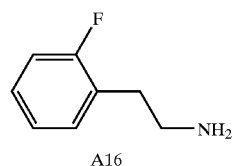
A16
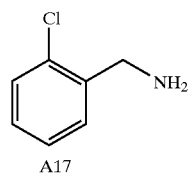
A17
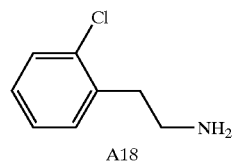
A18
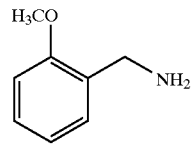
A19
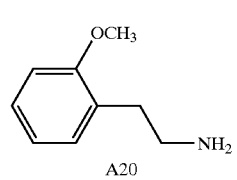
A20
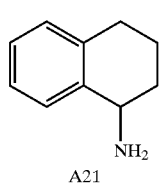
A21
TABLE 2-continued
The 60 building blocks used to assemble the parent library.
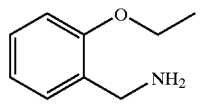
A22
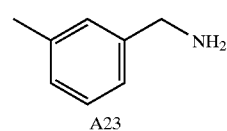
A23
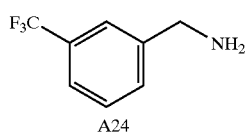
A24
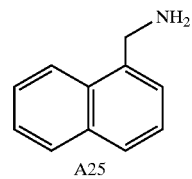
A25
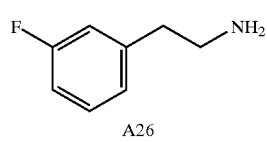
A26
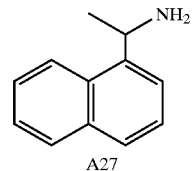
A27
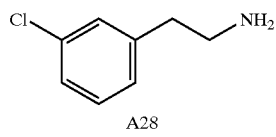
A28
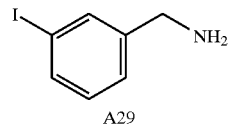
A29
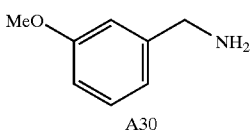
A30
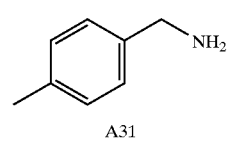
A31

TABLE 2-continued
The 60 building blocks used to assemble the parent library.
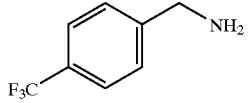
A32
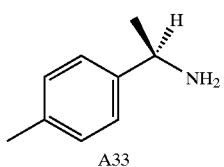
A33
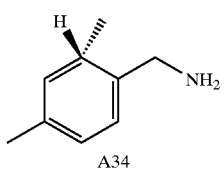
A34
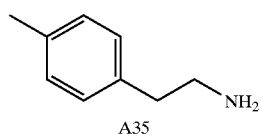
A35
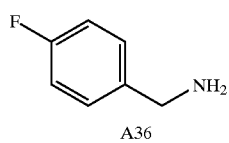
A36
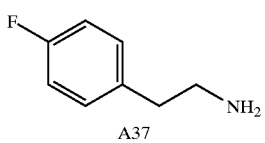
A37
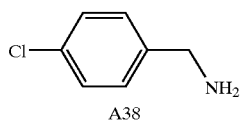
A38
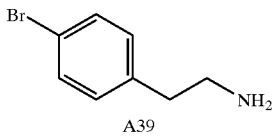
A39
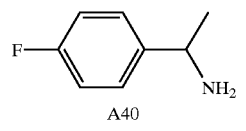
A40
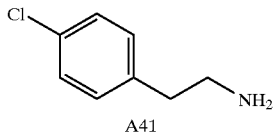
A41
TABLE 2-continued
The 60 building blocks used to assemble the parent library.
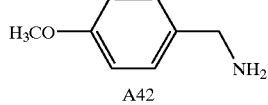
A42
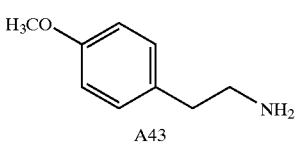
A43
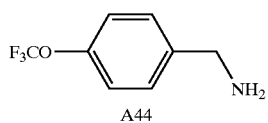
A44
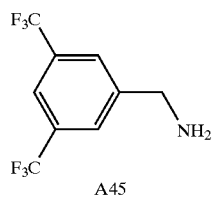
A45
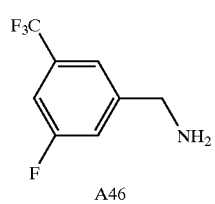
A46
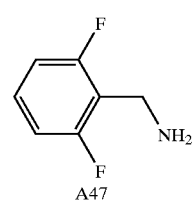
A47
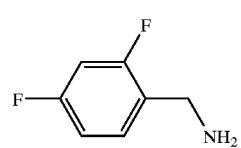
A48
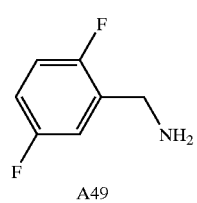
A49

TABLE 2-continued

The 60 building blocks used to assemble the parent library.

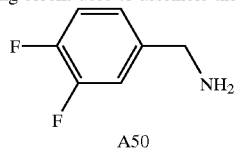
A50

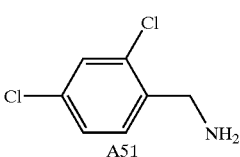
A51

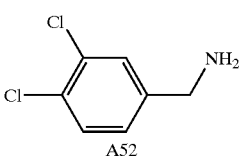
A52

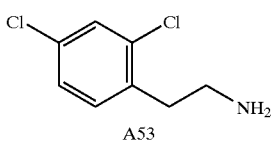
A53

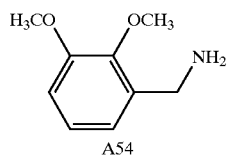
A54

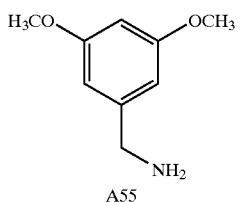
A55

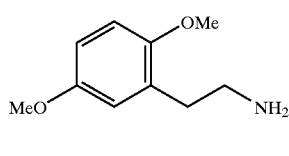
A56

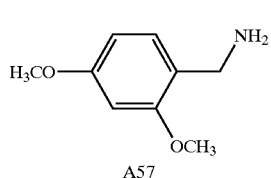
A57

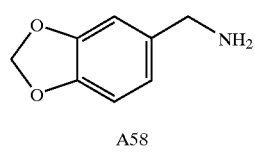
A58

TABLE 2-continued

The 60 building blocks used to assemble the parent library.

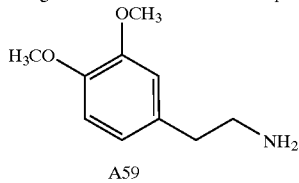
A59

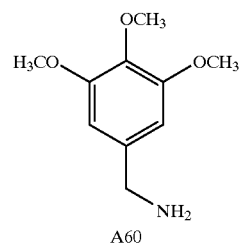
A60

The product mixture was purified by aqueous acid wash/extraction. The reaction and purification conditions employed were the same as described for SML. The collected yield was 70%. The ESI-MS spectrum is shown in FIG. 2A and a computer-generated MS spectrum is shown in FIG. 2B for comparison.

The $IC_{50}$ value of the CL34 parent library in MTT assays was 70 μg/ml. After the parent mixture library was discovered to be active, 60 positional scanning deconvolution libraries (Boger, D. L.; Jiang, W.; Goldberg, J. *J. Org. Chem.* 1999, 64, 7094–7100; (b) Dooley, C. T.; Houghten, R. A. *Life Sci.* 1993, 52, 1509; (c) Pinilla, C.; Appel, J. R.; Blanc, P.; Houghten, R. A. *Biotechniques,* 1992, 13, 901) were assembled in order to identify those building blocks essential for an active thiourea library as shown in Scheme 4.

Scheme 4

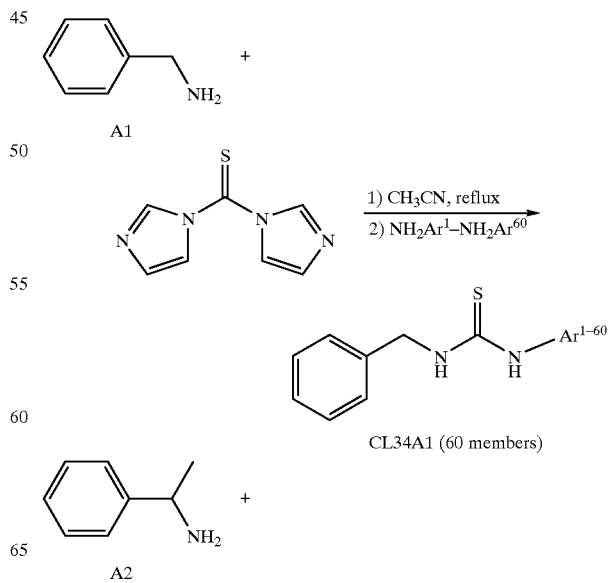

-continued

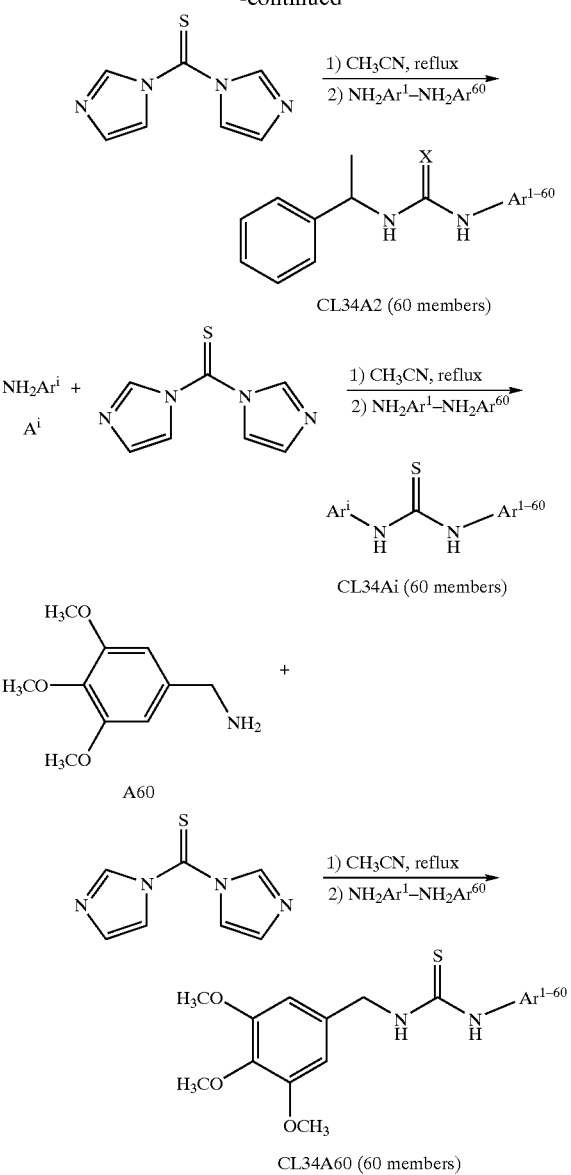

Each of the sublibraries is comprised of thiourea compounds that share an identical N substitution on one end and differ from each other by the variant N' substitution on the other end representing one of the 60 different building blocks shown in Table 2.

The solution phase combinatorial synthesis was accomplished using the Argonaut Quest 205 synthesizer, which can carry out 10 reactions in parallel. All of the reaction conditions used for glass flasks were readily adapted for the synthesizer, except reflux was replaced with temperature control at 81° C. (bp of acetonitrile) in sealed reaction vessels. Specifically, anhydrous acetonitrile (20 mL for each reaction vessel) was loaded in parallel in reaction vessels of Quest 205 synthesizer, which consists of 10 reaction vessels with 100-mL capacity each, followed by loading of TCDI (1.069 g, 6 mmol each reaction vessel). The reaction vessels were cooled down to 5° C. with circulating ice-water. Amines AL–A10 (Table 2) were dissolved in 20-mL anhydrous acetonitrile each separately, and added into the TCDI solutions dropwise, separately. The reaction vessels were heated up and maintained at 81° C. for 1 h in closed nitrogen-gas environment. The completion of the first substitution can be monitored with TLC. A stock solution of amines A1–A60 (Table 2) (1 mmol each) were dissolved in 200-mL acetonitrile. The amine mixture solution (20 mL each time) was added into every reaction vessel sequentially via syringes. The reaction vessels were heated up and maintained at 81° C. for 1 h. The same work-up was followed as in Example 1. A yellow gel was obtained with a 68–100% yield.

The biologic activity of the sublibraries was examined in standard MTT assays. The results, expressed as the $IC_{50}$ values (in $\mu g/ml$) are shown in Table 3.

TABLE 3

MTT Assay Results and Yields of Synthesis of the Deconvolution Libraries

| Sublibrary | $IC_{50}$, $\mu g/mL$ Nalm6 | Molt3 | Yield, % |
|---|---|---|---|
| CL34A1 | 41.05 | 51.2 | 94 |
| CL34A2 | 5.6 | 63.8 | 96 |
| CL34A3 | 8.7 | 28.4 | 100 |
| CL34A4 | 7.9 | 26.3 | 100 |
| CL34A5 | 19.0 | 8.6 | 92 |
| CL34A6 | 15.7 | 41.9 | 100 |
| CL34A7 | 52.9 | 45.4 | 93 |
| CL34A8 | 48.3 | 39.1 | 100 |
| CL34A9 | 17.8 | 22.2 | 100 |
| CL34A10 | 31.6 | 29.3 | 78 |
| CL34A11 | 38.3 | 35.6 | 81 |
| CL34A12 | 33.4 | 49.6 | 91 |
| CL34A13 | 43.7 | 42.0 | 100 |
| CL34A14 | 78.6 | 72.5 | 81 |
| CL34A15 | 76.3 | 95.7 | 83 |
| CL34A16 | 78.6 | 97.4 | 84 |
| CL34A17 | 41.3 | 76.8 | 83 |
| CL34A18 | 74.2 | 46.2 | 78 |
| CL34A19 | 41.5 | 40.5 | 73 |
| CL34A20 | 33.7 | 40.6 | 61 |
| CL34A21 | 37.0 | 39.1 | 100 |
| CL34A22 | 38.6 | 45.9 | 93 |
| CL34A23 | 60.2 | 98.5 | 91 |
| CL34A24 | 92.1 | 85.3 | 92 |
| CL34A25 | 44.7 | 29.2 | 84 |
| CL34A26 | 56.3 | >100 | 91 |
| CL34A27 | 25.9 | 20.5 | 90 |
| CL34A28 | 55.5 | 50.3 | 92 |
| CL34A29 | 44.2 | 45.6 | 71 |
| CL34A30 | 58.6 | >100 | 94 |
| CL34A31 | 56.3 | >100 | 89 |
| CL34A32 | 53.4 | >100 | 92 |
| CL34A33 | 44.8 | 64.5 | 89 |
| CL34A34 | 54.4 | >100 | 95 |
| CL34A35 | 93.1 | 99.3 | 99 |
| CL34A36 | 62.1 | >100 | 90 |
| CL34A37 | 45.3 | >100 | 96 |
| CL34A38 | 61.6 | 46.3 | 93 |
| CL34A39 | 49.5 | 53.6 | 94 |
| CL34A40 | 36.4 | >100 | 84 |
| CL34A41 | 73.2 | >100 | 91 |
| CL34A42 | 78.3 | >100 | 99 |
| CL34A43 | 84.8 | 98.4 | 100 |
| CL34A44 | 70.3 | 91.6 | 98 |
| CL34A45 | 20.8 | 21.0 | 94 |
| CL34A46 | 88.4 | 89.6 | 78 |
| CL34A47 | >100 | >100 | 68 |
| CL34A48 | 89.6 | 83.6 | 78 |
| CL34A49 | 97.4 | 95.6 | 93 |
| CL34A50 | 91.9 | >100 | 90 |
| CL34A51 | 95.6 | >100 | 31 |
| CL34A52 | 78.4 | 89.8 | 85 |

TABLE 3-continued

MTT Assay Results and Yields of Synthesis of the Deconvolution Libraries

| Sublibrary | IC$_{50}$, µg/mL | | Yield, % |
|---|---|---|---|
| | Nalm6 | Molt3 | |
| CL34A53 | 67.8 | 88.2 | 89 |
| CL34A54 | 70.8 | 71.6 | 88 |
| CL34A55 | 75.9 | 85.1 | 91 |
| CL34A56 | 10.6 | 32.0 | 99 |
| CL34A57 | 11.6 | 15.6 | 64 |
| CL34A58 | 48.3 | 91.5 | 98 |
| CL34A59 | 62.1 | 71.5 | 86 |
| CL34A60 | 63.3 | 57.6 | 85 |

The results in Table 2 indicate that sublibraries CL34A2, CL34A3, CL34A4, and CL34A5, containing 60 compounds each, have significant cytotoxic activity with IC50 values<10 µg/ml. Sublibraries CL34A56 and CL34A57 were also cytotoxic, with slightly higher IC50 values. 21 individual compounds (6 symmetrical and 15 asymmetrical compounds) using the active building blocks of these 6 sublibraries were synthesized (Chart 4).

Chart 4. The Individual Compounds Synthesized

1) Group 1 (IC$_{50}$<10 µg/mL, 10 compounds)

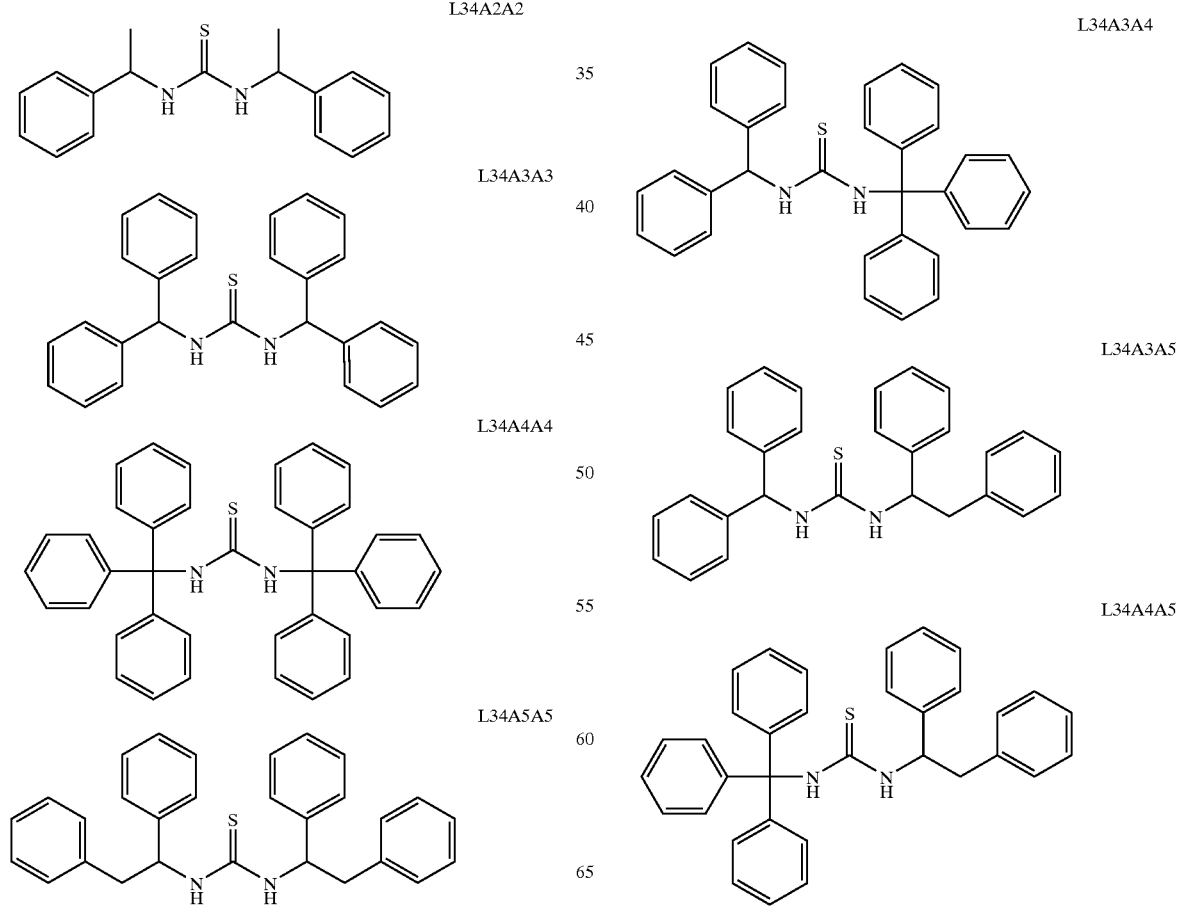

L34A56A56
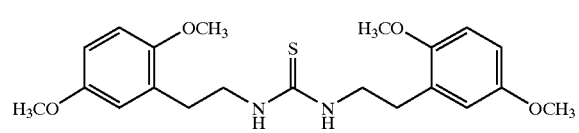

L34A57A57
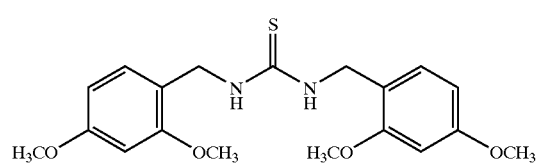

L34A2A56
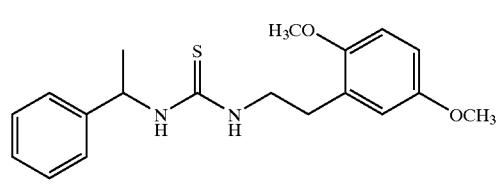

L34A2A57
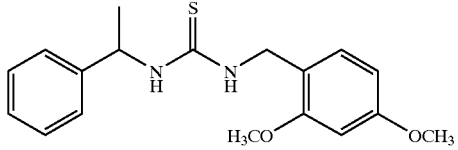

L34A3A56
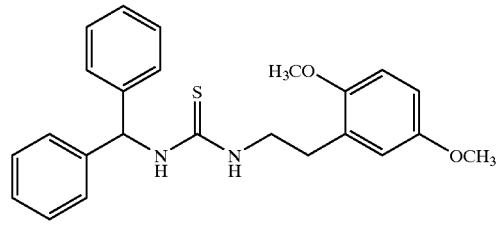

L34A3A57
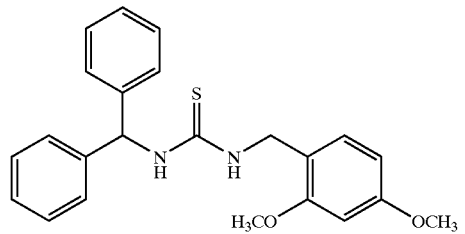

L34A4A56
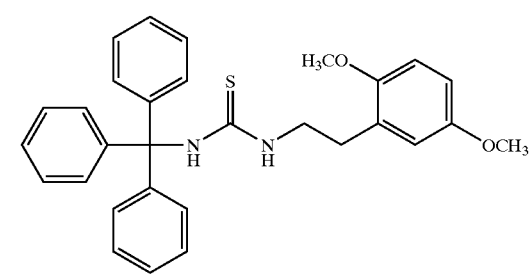

L34A4A57
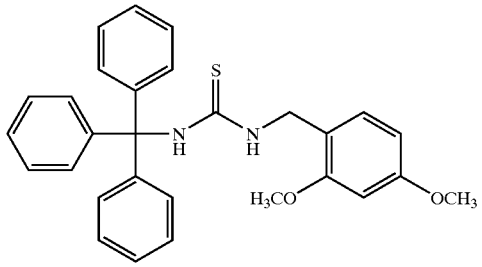

L34A5A56
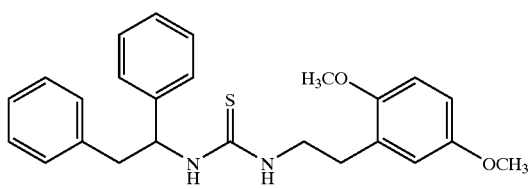

L34A5A57
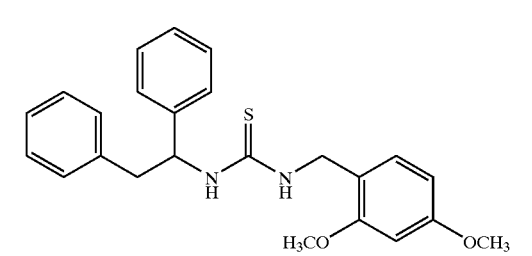

L34A56A57
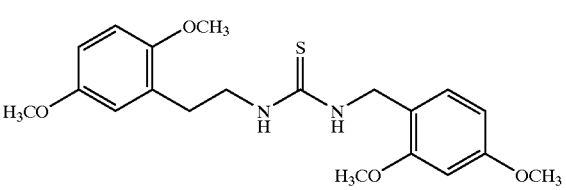

Specifically, anhydrous acetonitrile (10 mL for each reaction vessel) was loaded in parallel in reaction vessels of Quest 205 synthesizer, followed by loading of TCDI (0.535 g, 3 mmol each reaction vessel). The reaction vessels were cooled down to 5° C. with circulating ice-water. Amines A2, A3, A5, A56 and A57 (6 mmol each) were dissolved in 20-mL anhydrous acetonitrile each separately, and added into #1–#5 of the TCDI solutions, separately. Amine A2 (3 mmol each in three round-bottomed flasks) was dissolved in anhydrous acetonitrile (10-mL each) separately, and added into TCDI solutions in reaction vessels #6–#8 dropwise at 5° C. Amine A3 (3 mmol each in two round-bottomed flasks) was dissolved in anhydrous acetonitrile (10-mL each) separately, and added into TCDI solutions in reaction vessels #9 and #10 dropwise at 5° C. The reaction vessels #6–#10 were heated up to and maintained at 81° C. for one hour (The temperature of the two banks, #1–#5 and #6–#10, can be controlled separately). Amines A3, A4 and A5 were dissolved in 10-mL acetonitrile each in three round-bottomed flasks, and added into reaction vessels #6–#8 dropwise at 5° C. Amines A4 and A5 were dissolved in 10-mL acetonitrile each in two round-bottomed flasks, and added into reaction vessels #9 and #10 separately at 5° C. The reaction vessels were heated up to and maintained at 81° C. for one hour. The same work-up was followed as in Example 1.

These 21 compounds were tested for cytotoxic activity against Nalm6 leukemia cell line using MTT assays. The results are presented in Table 4. The most active compounds were L34A5A5 (1,3-bis(1,2-diphenylethyl)-2-thiourea) and L34A3A5 (1-(1,2-diphenylethyl)-3-(diphenylmethyl)-2-thiourea). L34A2A5 and L34A3A56 ranked second best.

TABLE 4

MTT Assay Results and Yields for the Lead Compounds

| Compounds | ED$_{50}$, µg/mL Nalm6 | Yield, % |
|---|---|---|
| Group 1 | | |
| L34A2A2 | 50 | 76 |
| L34A3A3 | >100 | 78 |
| L34A4A4 | 30 | 67 |
| L34A5A5 | <10 | 68 |
| L34A2A3 | 50 | 67 |
| L34A2A4 | 50 | 80 |
| L34A2A5 | 25 | 68 |
| L34A3A4 | >50 | 82 |
| L34A3A5 | <10 | 85 |
| L34A4A5 | 50 | 97 |
| Group 2 | | |
| L34A56A56 | 50 | 78 |
| L34A57A57 | 30 | 75 |
| L34A2A56 | >50 | 85 |
| L34A2A57 | >50 | 82 |
| L34A3A56 | 25 | 82 |
| L34A3A57 | 30 | 81 |
| L34A4A56 | 50 | 72 |
| L34A4A57 | 30 | 63 |
| L34A5A56 | 50 | 82 |
| L34A5A57 | 30 | 82 |
| L34A56A57 | >50 | 92 |

The physicochemical data for the two most active compounds are as follows:

1,3-Bis(1,2-diphenylethyl)-2-thiourea (L34A5A5). A white powder (0.887 g, 68% yield) was obtained as the desired product. $^1$H NMR (CDCl$_3$, 300 MHz) d 7.31–6.80 (m, 20H), 6.08 (bs, 2H), 5.08 (bs, 2H), 3.00 (d, J=6.6 Hz, 4H); $^{13}$C NMR (CDCl$_3$, 75 MHz) d 180., 140.0, 136.1, 129.3, 129.1, 128.7, 128.4, 128.2, 126.5, 126.2, 107.2, 60.0, 59.3, 43.1; m/z (MALDI-TOF) 437.1 (C$_{29}$H$_{28}$N$_2$S+H$^+$ requires 437.6); UV-vis 1$_{max}$ 202, 208, 253 nm; HPLC retention time 37.7 min, purity 98%.

1-(1,2-Diphenylethyl)-3-(diphenylmethyl)-2-thiourea (L34A3A5). A white powder (0.981 g, 77% yield) was obtained as the desired product. $^1$H NMR (CDCl$_3$, 300 MHz) d 7.35–7.15 (m, 15H), 6.91 (m, 5H), 6.16 (m, 3H), 5.22 (bs, 1H), 3.04 (m, 2H); m/z (MALDI-TOF) 422.4 (C$_{28}$H$_{26}$N$_2$S$^+$ requires 422.6); UV-vis 1$_{max}$ 202, 206, 253 nm; HPLC retention time 33.3 min, purity 92%.

Example 3

Synthesis of Urea Mixture Libraries

Figure 3B:
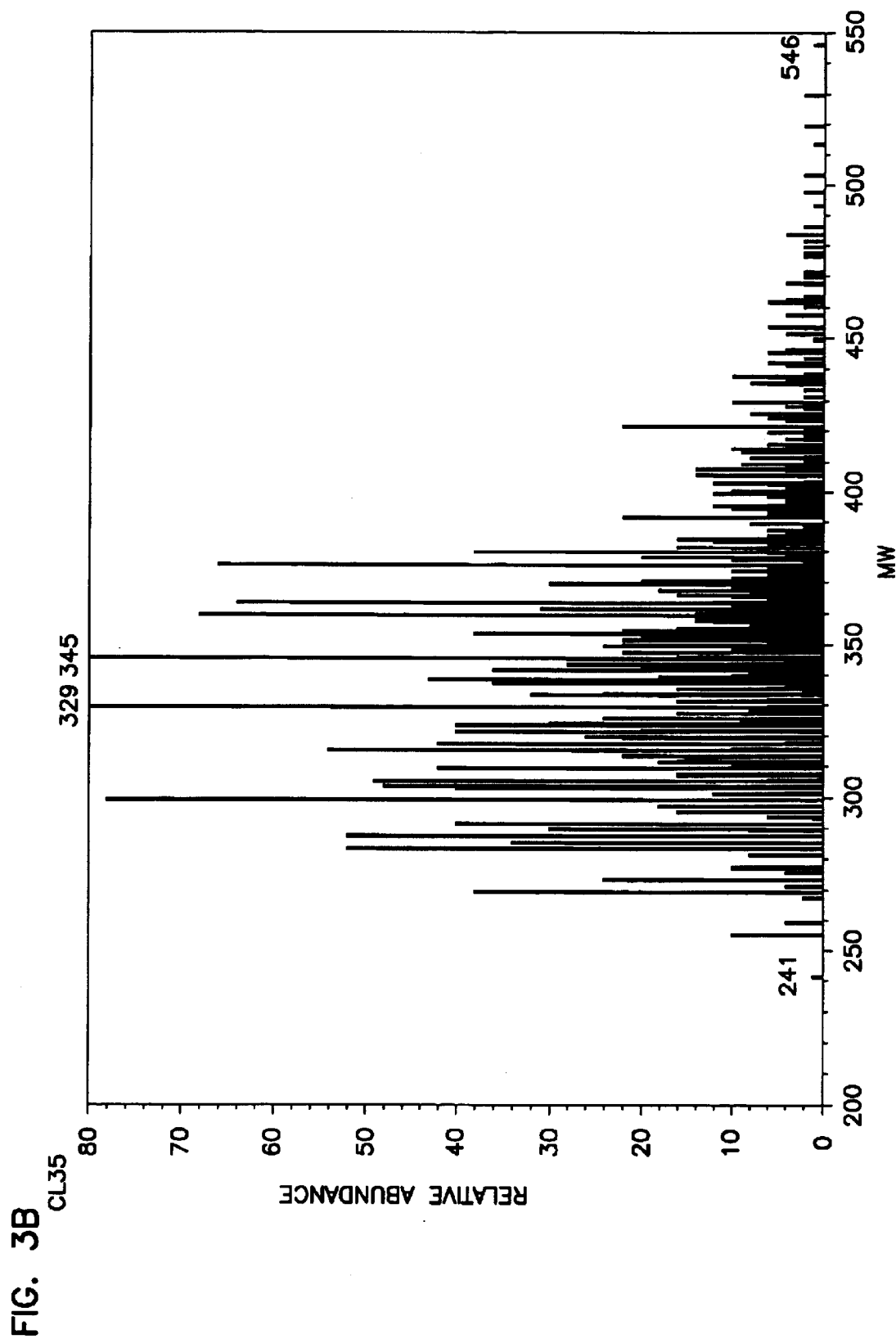
FIGS. 3A and B: are ESI mass spectrum of CL35 (FIG. 3A) and a computer generated mass spectrum (FIG. 3B) of CL35 for comparison.

A mixture containing 1830 urea compounds was synthesized in one step depicted in Scheme 5 from carbonyldiimidazole and 60 commercially-available amines shown in FIG. 3, as described for thiourea compounds in Example 2. Sixty positional scanning deconvolution libraries were synthesized for the identification of active components. FIG. 3A shows the ESI-MS spectrum of CL35. FIG. 3B shows a computer-generated MS spectrum of CL35 for comparison.

Scheme 5

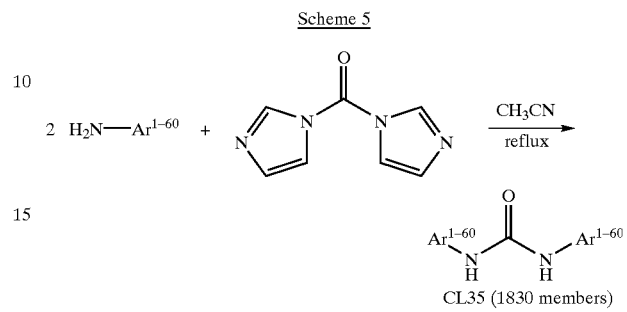

CL35 (1830 members)

The MTT assay results for these sublibraries are shown in Table 5.

TABLE 5

MTT Assay Results of the Deconvolution Libraries

| Sublibrary | IC$_{50}$, µg/mL Nalm6 | Molt3 |
|---|---|---|
| CL35A1 | >100 | >100 |
| CL35A2 | >100 | >100 |
| CL35A3 | >100 | >100 |
| CL35A4 | 36.9 | 24.1 |
| CL35A5 | 20.6 | 22.9 |
| CL35A6 | 33.3 | 26.2 |
| CL35A7 | 95.6 | >100 |
| CL35A8 | 90.2 | 91.3 |
| CL35A9 | 37.9 | 31.8 |
| CL35A10 | 81.4 | 96.4 |
| CL35A11 | 65.3 | 95.1 |
| CL35A12 | 74.4 | 57.9 |
| CL35A13 | 24.8 | 36.7 |
| CL35A14 | 60.3 | 64.1 |
| CL35A15 | 86.2 | >100 |
| CL35A16 | 81.5 | >100 |
| CL35A17 | 71.2 | 96.1 |
| CL35A18 | 84.2 | 90.5 |
| CL35A19 | 81.2 | 95.6 |
| CL35A20 | 62.5 | 68.2 |
| CL35A21 | 70.1 | 66.3 |
| CL35A22 | 68.3 | 66.2 |
| CL35A23 | 88.2 | 81.5 |
| CL35A24 | 70.6 | 95.4 |
| CL35A25 | 58.1 | 56.2 |
| CL35A26 | 60.4 | 66.2 |
| CL35A27 | 23.4 | 23.6 |
| CL35A28 | 45.8 | 71.5 |
| CL35A29 | 47.8 | 50.3 |
| CL35A30 | 85.6 | >100 |
| CL35A31 | 70.2 | 62.5 |
| CL35A32 | 66.3 | 60.5 |
| CL35A33 | 48.1 | 60.2 |
| CL35A34 | 37.2 | 46.5 |
| CL35A35 | 66.3 | >100 |
| CL35A36 | 90.5 | 91.2 |
| CL35A37 | 49.6 | 96.5 |
| CL35A38 | 42.5 | 70.2 |
| CL35A39 | 36.2 | 48.9 |
| CL35A40 | 70.2 | 94.0 |
| CL35A41 | 49.2 | 37.9 |
| CL35A42 | 70.5 | 78.2 |
| CL35A43 | 75.6 | 79.1 |
| CL35A44 | 73.6 | 70.5 |
| CL35A45 | 44.7 | 32.3 |

TABLE 5-continued

MTT Assay Results of the Deconvolution Libraries

| | IC$_{50}$, µg/mL | |
|---|---|---|
| Sublibrary | Nalm6 | Molt3 |
| CL35A46 | 53.2 | 55.8 |
| CL35A47 | >100 | >100 |
| CL35A48 | >100 | >100 |
| CL35A49 | 98.1 | 92.6 |
| CL35A50 | 96.8 | 90.2 |
| CL35A51 | 18.9 | 38.3 |
| CL35A52 | 25.8 | 48.3 |
| CL35A53 | 27.1 | 29.7 |
| CL35A54 | 62.5 | 60.4 |
| CL35A55 | 56.8 | 50.6 |
| CL35A56 | 53.4 | 55.9 |
| CL35A57 | 42.6 | 52.6 |
| CL35A58 | 43.4 | 40.2 |
| CL35A59 | 66.8 | 70.2 |
| CL35A60 | >100 | >100 |

Sublibraries CL35A2, CL35A3, CL35A4, and CL35A5, containing 60 compounds each, were the most biologically active.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

The content of all publications, patents, and patent documents described and cited herein is incorporated by reference as if fully set forth. The invention described herein may be modified to include alternative embodiments. All such obvious alternatives are within the spirit and scope of the invention, as claimed below.

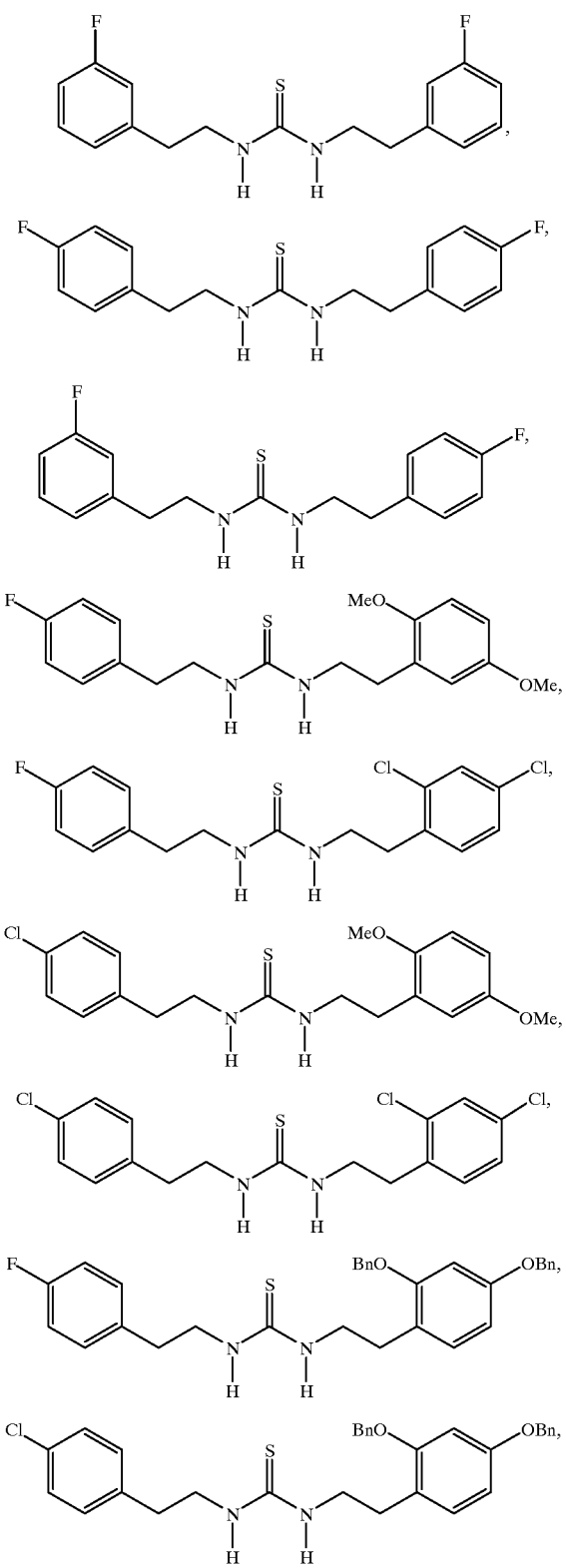
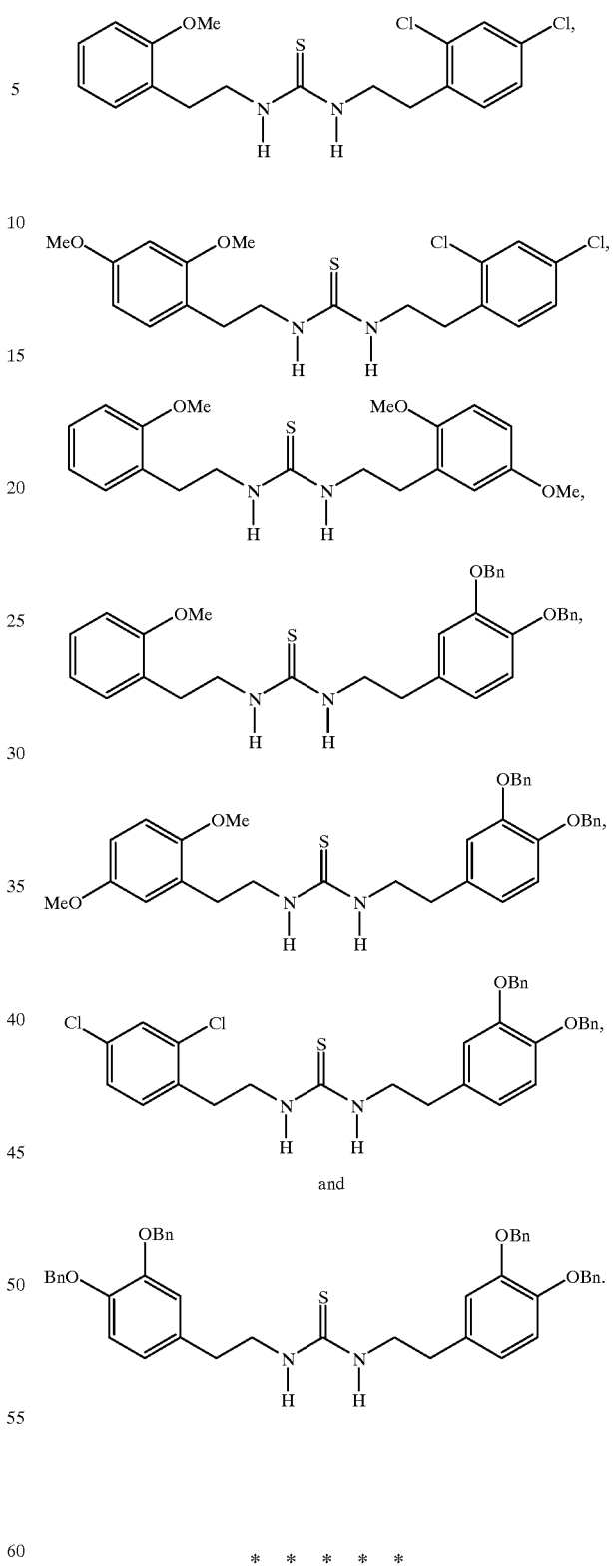

What is claimed is:

1. A compound selected from the group consisting of:

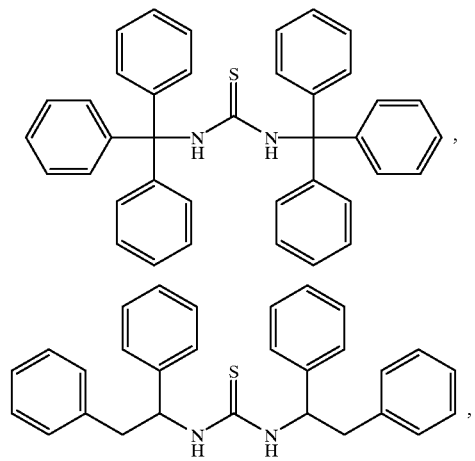

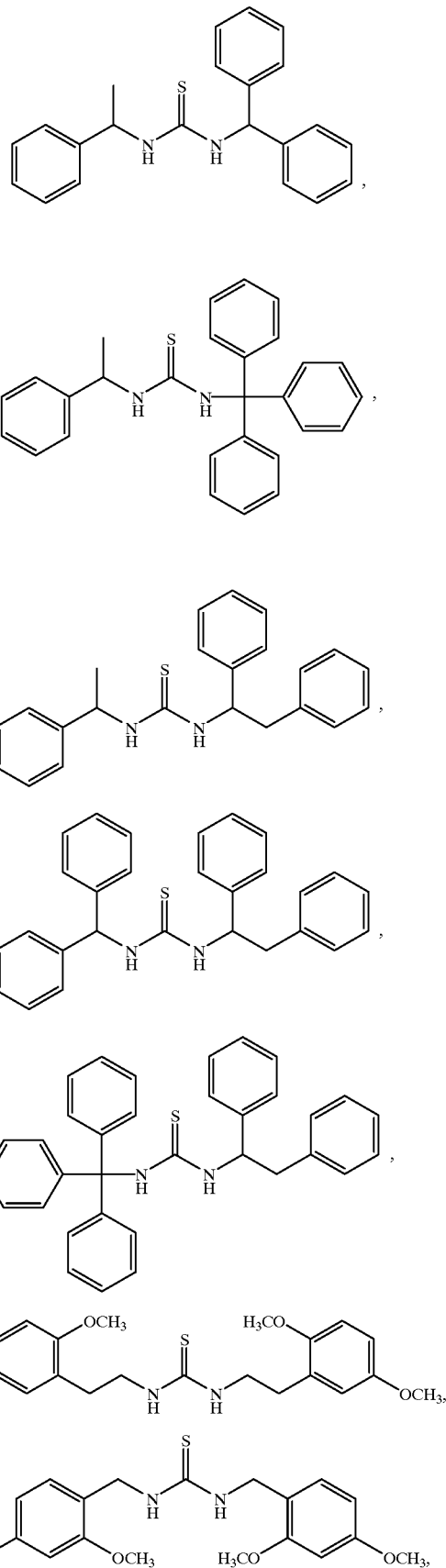

-continued